US008834865B2

(12) United States Patent
Becker et al.

(10) Patent No.: US 8,834,865 B2
(45) Date of Patent: Sep. 16, 2014

(54) DELIVERY SYSTEM FOR CO-FORMULATED ENZYME AND SUBSTRATE

(75) Inventors: Nathaniel T. Becker, Hillsborough, CA (US); Michael Stoner, San Jose, CA (US); Mee-Young Yoon, Harborside, ME (US)

(73) Assignee: Danisco US Inc., Palo Alto, CA (US)

( * ) Notice: Subject to any disclaimer, the term of this patent is extended or adjusted under 35 U.S.C. 154(b) by 0 days.

(21) Appl. No.: 13/132,069

(22) PCT Filed: Nov. 3, 2009

(86) PCT No.: PCT/US2009/063085

§ 371 (c)(1), (2), (4) Date: Aug. 26, 2011

(87) PCT Pub. No.: WO2010/062745

PCT Pub. Date: Jun. 3, 2010

(65) Prior Publication Data

US 2011/0300201 A1 Dec. 8, 2011

Related U.S. Application Data

(60) Provisional application No. 61/110,832, filed on Nov. 3, 2008.

(51) Int. Cl.
*A61K 38/54* (2006.01)
*C11D 3/386* (2006.01)
*C11D 17/00* (2006.01)

(52) U.S. Cl.
CPC ........ *C11D 17/0039* (2013.01); *C11D 3/38672* (2013.01); *C11D 3/38681* (2013.01); *C11D 3/386* (2013.01)
USPC .......... 424/94.3; 435/197; 435/201; 435/195; 435/219; 424/94.1; 424/94.5; 514/557

(58) Field of Classification Search
None
See application file for complete search history.

(56) References Cited

U.S. PATENT DOCUMENTS

| | | | | |
|---|---|---|---|---|
| 4,898,781 | A | 2/1990 | Onouchi et al. | |
| 5,281,355 | A | 1/1994 | Tsaur et al. | |
| 5,281,357 | A | 1/1994 | Morgan et al. | |
| 5,324,445 | A | 6/1994 | Langley et al. | |
| 5,441,660 | A | 8/1995 | Tsaur et al. | |
| 6,329,332 | B1 | 12/2001 | Borneman et al. | |
| 2008/0025960 | A1 | 1/2008 | Kumar et al. | |
| 2008/0145353 | A1 * | 6/2008 | Amin et al. | 424/94.6 |
| 2008/0196173 | A1 | 8/2008 | Wang et al. | |

FOREIGN PATENT DOCUMENTS

| | | |
|---|---|---|
| EP | 1064359 | 9/1999 |
| EP | 1141321 | 6/2000 |
| JP | S62-220191 | 9/1997 |
| JP | S63-105098 | 5/1998 |
| WO | WO93/22417 | 11/1993 |
| WO | WO 97/24177 | 7/1997 |
| WO | WO 00/05349 | 2/2000 |
| WO | WO 00/63336 | 10/2000 |
| WO | WO 2008/076322 | 6/2008 |

OTHER PUBLICATIONS

Hale and Marham, The Harper Collins Dictionary of Biology, Harper Perennial, NY (1991).

Kirk-Othmer Encyclopedia of Chemical Technology "Microencapsulation" 2005.

Singleton and Sainsbury, Dictionary of Microbiology and Molecular Biology, 2d Ed., John Wiley and Sons, NY 1994).

International Patent Application No. PCT/US2009/063085 Search Report dated Mar. 18, 2010.

Sakai et al., Advances in Applied Microbiology (1993) 39 pp. 213-294.

International Preliminary Report on Patentability for International Application No. PCT/US2009/063085 dated May 3, 2011.

* cited by examiner

*Primary Examiner* — Jon P Weber
*Assistant Examiner* — Teresa E Knight
(74) *Attorney, Agent, or Firm* — Danisco US Inc.

(57) ABSTRACT

The invention provides methods, compositions, systems, and kits that include an enzyme/substrate co-delivery system. The liquid delivery system includes at least one enzyme encapsulated in a water-soluble polymeric matrix and a substrate for the enzyme in a carrier liquid in which the polymeric matrix is insoluble. When water is added, the polymeric matrix is solubilized and enzyme is released from the matrix, permitting catalytic action upon the substrate.

26 Claims, 4 Drawing Sheets

DELIVERY SYSTEM FOR CO-FORMULATED ENZYME AND SUBSTRATE

PRIORITY

The present application claims priority under 35 USC §371 to International Application No. PCT/US2009/063085, filed Nov. 3, 2009, which claims the benefit of U.S. Provisional Patent Application Ser. No. 61/110,832, filed on Nov. 3, 2008, each of which is herein incorporated by reference.

SEQUENCE LISTING

The sequence listing submitted via EFS, in compliance with 37 C.F.R. §1.52(e), is incorporated herein by reference. The sequence listing text file submitted via EFS contains the file "31159US2_SequenceListing", created on May 31, 2011, which is 7,449 bytes in size.

FIELD OF THE INVENTION

The invention relates to liquid formulations for co-delivery of enzymes and substrates in which at least one enzyme is encapsulated in a polymeric matrix.

BACKGROUND

In delivery of enzyme/substrate systems, two problems generally arise. The first problem is that optimal effectiveness depends on maintaining the proper enzyme:substrate ratio. The second problem is that enzyme must be physically isolated from its substrate until the reaction is desired. One way to overcome these problems is to package enzyme separately from substrate and combine them at the point of use. However, this approach is inconvenient, complicated, and can result in blending errors at the point of use. It can also be costly since the enzyme often must be formulated with stabilizing substances. Another way to overcome these problems is to provide a blend of dry enzyme and dry substrate, thus achieving physical isolation while maintaining the proper enzyme-to-substrate ratio. However, it is frequently desirable or necessary to provide a liquid formulation for use in processes which are not set up to handle powders, granules, or other solid products. An alternative approach is needed.

A co-formulation approach would be desirable, with enzyme and substrate combined in the same container. This would allow a manufacturer to control the enzyme:substrate ratio, resulting in cost savings on formulation ingredients, and would provide a simple, convenient, and "ready-to-use" product to the consumer. In some cases, combining enzyme and substrate in the same liquid formulation could mitigate toxicity concerns (e.g., environmental risks posed by laccase mediators could be substantially reduced if they could be handled and transported in the same container as the laccase enzyme itself).

Ounichi (U.S. Pat. No. 4,898,781) and Aronson (U.S. Pat. No. 5,281,355) teach encapsulation of enzymes for laundry and home care applications where the resulting product contains only an enzyme, and does not contain a reactive substrate. It would be desirable to produce a liquid formulation containing both enzyme and substrate, with the enzyme isolated from the reactive substrate. Applications in which such a co-formulation would be useful include, but are not limited to, enzymatic bleaching systems, for example, using a perhydrolase enzyme with an ester substrate, and enzymatic dyeing systems, for example, using a laccase enzyme and a dye precursor substrate.

BRIEF SUMMARY OF THE INVENTION

In one aspect, the invention provides a liquid delivery system for co-formulated enzyme and substrate, wherein the delivery system is a composition containing an enzyme and a substrate for the enzyme, wherein the enzyme is encapsulated in a water-soluble polymeric matrix. The substrate is in a substantially non-aqueous liquid phase (i.e., less than about 5%, less than about 1%, or less than about 0.5% water) in contact with the polymeric matrix that contains the enzyme, wherein the polymer is not soluble in the liquid phase. The enzyme retains catalytic potential in the polymeric matrix but substantially does not react with the substrate in the composition for at least 10 days at 25° C. After addition of water to the composition, the polymeric matrix is solubilized, releasing the enzyme, permitting catalytic reaction with the substrate to occur.

In some embodiments, the composition contains one or more enzymes selected from proteases, cellulases, amylases, pectinases, perhydrolases, peroxidases, carbohydrate oxidases, phenol oxidizing enzymes, cutinases, lipases, hemicellulases, xylanases, mannanases, catalases, and laccases, and mixtures thereof. In some embodiments, the composition contains two or more enzymes encapsulated in the same polymeric matrix. In some embodiments, the composition contains two or more enzymes encapsulated in separate polymeric matrices. In some embodiments, the composition contains two or more enzymes encapsulated in the same polymeric matrix and at least one enzyme encapsulated in a separate polymeric matrix.

In some embodiments, the composition contains at least one surfactant.

In some embodiments, the polymeric matrix is selected from polyvinyl alcohol, methylcellulose, hydroxypropyl methylcellulose, polyvinyl pyrrolidone, guar gum, and derivatives or co-polymers thereof. A suitable polymer for use in the compositions provided herein is one in which an enzyme may be encapsulated and which is not soluble in water.

In some embodiments, the enzyme-containing polymeric matrix is in the form of particles suspended in a substantially non-aqueous liquid containing the substrate. In one embodiment, the particles are held in suspension by a suspending aid. In some embodiment, the liquid suspension is in a container that contains an amount of enzyme and substrate sufficient for and/or intended for a single use (i.e., a single dose) in an application in which the enzyme/substrate reaction is useful, wherein the container may be opened to dispense the liquid, for example, by opening a cap or lid. In some embodiments, the liquid suspension is in a resealable container that contains an amount of enzyme and substrate sufficient for and/or intended for use multiple times (i.e., multiple doses), which allows for repeated dispensing of the suspension by opening and closing a container cap, opening and closing a valve or dispensing port, or the like. In some embodiments, the enzyme-containing polymeric matrix is in the form of a closed, i.e., sealed, container, such as a pouch or sachet, and the substrate is in a substantially non-aqueous liquid inside the polymeric container.

The substrate is solubilized or dispersed in a substantially non-aqueous liquid phase, which may include a non-aqueous liquid (carrier fluid). Examples of carrier fluids include, but are not limited to, glycols, nonionic surfactants, alcohols, polyglycols, acetate esters, or a mixture thereof. A liquid or solid substrate may be combined with one or more carrier fluid and may be either miscible with or suspended in the carrier fluid(s). In some embodiments, the carrier fluid contains salt or a pH buffer added to create conditions suitable for increased solubilization of the substrate and/or reduced solubilization of the encapsulating polymer. In some embodiments, the carrier fluid is a substrate for the enzyme, for example, a propylene glycol diacetate carrier fluid may serve as a substrate for a perhydrolase enzyme encapsulated in a polymeric matrix which is insoluble in propylene glycol diacetate, e.g., polyvinyl alcohol, methyl cellulose, hydroxypropl methyl cellulose, polyvinyl pyrrolidone). In many embodiments, the delivery exhibits increased stability compared to a comparable delivery system lacking the polymer.

In one embodiment, the enzyme is a perhydrolase and the substrate is an ester substrate, such as, for example, an acetate ester, e.g., propylene glycol diacetate. In some embodiments, the ester substrate is propylene glycol diacetate, and the polymer comprising the perhydrolase enzyme is in the form of particles suspended in the propylene glycol diacetate or in the form of a closed container surrounding the propylene glycol diacetate, i.e., the propylene glycol diacetate is enclosed within the polymeric container.

In some embodiments, the enzyme is a perhydrolase, the substrate is an ester substrate, the composition further comprises a hydrogen peroxide generating compound, for example, selected from sodium percarbonate, sodium perborate, and urea hydrogen peroxide, and a peracid is produced after water is added to the composition. In some embodiments, the peracid is selected from peracetic acid, pernonanoic acid, perpropionic acid, perbutanoic acid, perpentanoic acid, and perhexanoic acid. In some embodiments, the ester substrate is propylene glycol diacetate and the hydrogen peroxide generating compound is suspended in the propylene glycol diacetate.

In some embodiments, the enzyme is a perhydrolase enzyme and the composition contains substrates for producing mono- and diglycerides (e.g., an acyl donor and alcohol acceptor) or a sorbitan ester (e.g., an acyl donor and sorbitan). In some embodiments, the enzyme is a perhydrolase enzyme and the composition contains substrates for producing a fragrant ester, for example, a benzyl ester (e.g., an acyl donor and a volatile alcohol, for example benzyl alcohol).

In some embodiments, the enzyme is a phenol oxidizing enzyme, such as a laccase enzyme, and the substrate is a laccase mediator, for example, selected from 2,2'-azino-bis (3-ethylbenzothiazoline-6-sulfonate), syringamide, and syringonitrile.

In various aspects, the invention provides a composition for use in an application in which an enzymatic activity is useful, for example, a detergent composition, a textile processing composition, or a personal care composition, wherein the composition contains an enzyme and a substrate for the enzyme, wherein the enzyme is encapsulated in a water-soluble polymeric matrix and wherein the enzyme-containing polymeric matrix is in contact with and insoluble in a substantially non-aqueous liquid solution or suspension containing the substrate, as described herein.

In another aspect, the invention provides a kit containing a delivery system for co-formulated enzyme and substrate as described herein or a composition containing the delivery system, and packaging. In some embodiments, the kit further comprises instructions for use in a method, for example, a decontamination method, a cleaning method, a textile processing method, or a personal care method. In some embodiments, the kit further comprises instructions for incorporating the delivery system into a formulated composition for use in a method in which catalytic activity of the enzyme upon the substrate is useful, for example, a detergent composition, a textile processing composition, or a personal care composition.

In another aspect, the invention provides a method for decontamination, comprising: (a) adding a perhydrolase-containing composition as described herein to water in the presence of a hydrogen peroxide source and mixing, thereby generating an aqueous peracid solution; and (b) contacting an item comprising a contaminant with the solution, thereby reducing the concentration of the contaminant. In some embodiments, the contaminant comprises a toxin selected from botulinum toxin, anthracis toxin, ricin, scombroid toxin, ciguatoxin, tetradotoxin, mycotoxins, or a combination thereof. In some embodiments, the contaminant comprises a pathogen selected from a bacterium, a virus, a fungus, a parasite, a prion, or a combination thereof. In some embodiments, the item is selected from a hard surface, a fabric, a food, a feed, an apparel item, a rug, a carpet, a textile, a medical instrument, and a veterinary instrument. In some embodiments, the water is sterilized. In some embodiments, contacting the item to be decontaminated is performed at high temperature.

In another aspect, the invention provides a method for bleaching a textile, comprising: (a) adding a perhydrolase-containing composition as described herein to water in the presence of a hydrogen peroxide source and mixing, thereby generating an aqueous peracid solution; and (b) contacting a textile with the solution for a length of time and under conditions suitable to permit measurable whitening of the textile, thereby producing a bleached textile.

In another aspect, the invention provides a method for cleaning, comprising contacting an article comprising a stain with a detergent composition as described herein in the presence of added water, wherein at least a portion of the stain is removed.

In another aspect, the invention provides a method for bleaching a textile, comprising contacting a textile with a phenol oxidizing enzyme (e.g., laccase) containing composition as described herein in the presence of added water for a length of time and under conditions to permit measurable whitening of the textile, wherein the composition comprises a mediator that effects whitening of the textile, thereby producing a bleached textile.

In another aspect, the invention provides a method for changing the color of a textile, comprising contacting a textile with a phenol oxidizing enzyme (e.g., lactase) containing composition as described herein in the presence of added water for a length of time and under conditions suitable to permit a measurable change of color in the textile, wherein the composition comprises a mediator that effects a change of color in the textile under the conditions used, thereby producing a textile with a change in color.

In another aspect, the invention provides a method for hair dyeing, comprising contacting hair with a phenol oxidizing enzyme (e.g., laccase) containing composition as described herein in the presence of added water for a length of time and under conditions suitable to permit a measurable change of color in the hair, wherein the composition comprises a mediator that effects a change of color in the hair under the conditions used, thereby producing hair with a change in color.

In another aspect, the invention provides a method for pulp or paper bleaching and/or delignification, comprising contacting pulp or paper with a phenol oxidizing enzyme (e.g., laccase) containing composition as described herein in the presence of added water for a length of time and under conditions suitable to permit measurable change of color and/or lignin content of the pulp or paper, wherein the composition comprises a mediator that effects the change of color and/or lignin content, thereby producing pulp or paper with a change of color and/or lignin content.

In another aspect, the invention provides a method for enzymatic activation of wood fibers to produce wood composites, comprising contacting wood with a phenol oxidizing enzyme (e.g., laccase) containing composition as described herein in the presence of added water for a length of time and under conditions suitable to permit measurable change of wood composite yield, wherein the composition comprises a mediator that effects the change of yield of wood composite, thereby producing wood with a change in wood fiber bonding.

In another aspect, the invention provides a method for treating waste water, comprising contacting waste water effluent with a phenol oxidizing enzyme (e.g., laccase) containing composition as described herein in the presence of added water for a length of time and under conditions suitable to permit a measurable decrease in phenol concentration in the waste water, wherein the composition comprises a mediator that effects the decrease in phenol concentration, thereby producing waste water effluent with a decrease in phenol content.

DETAILED DESCRIPTION

Figure 1:
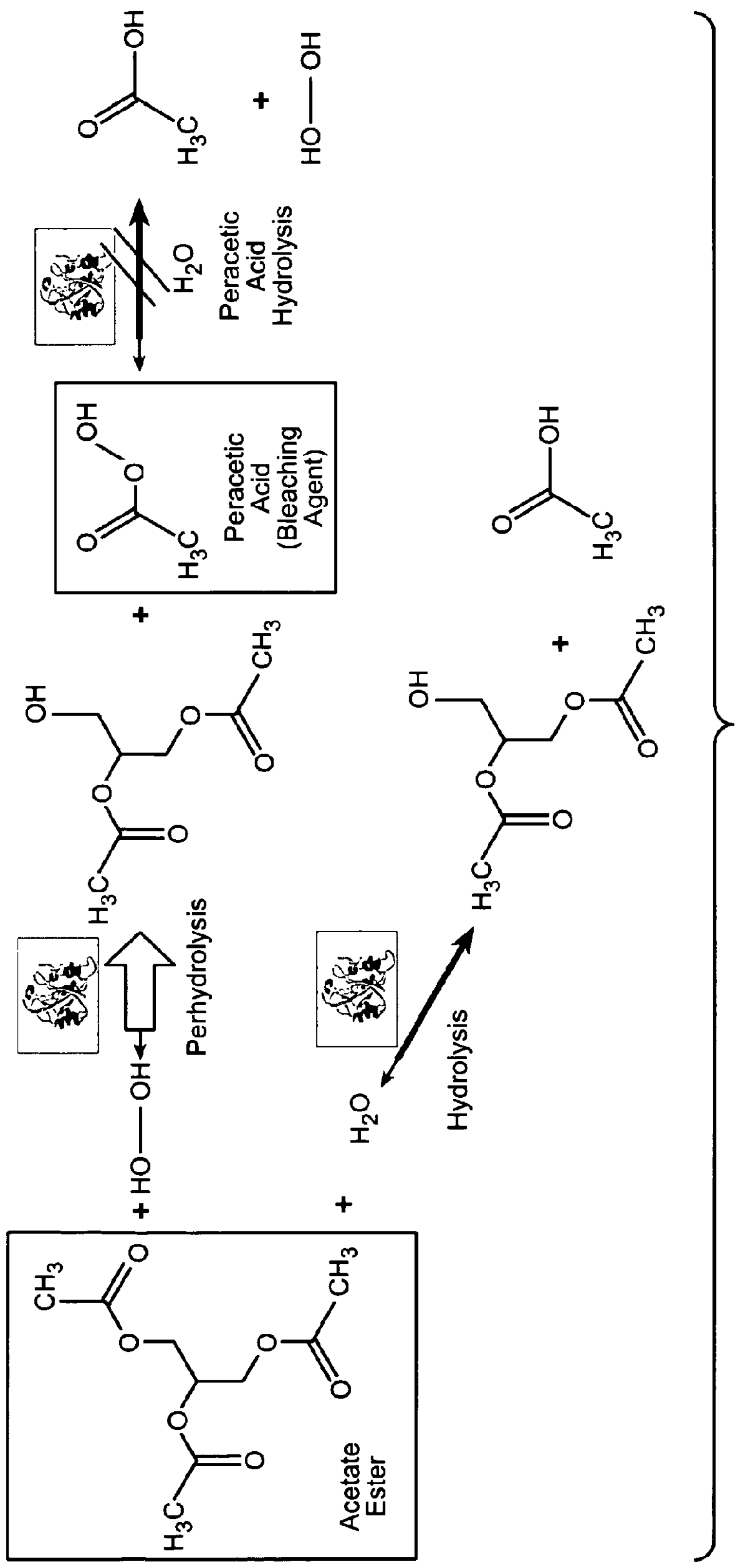
FIG. 1 schematically depicts reactions catalyzed by a perhydrolase enzyme.

The invention provides a delivery system for co-formulated enzyme and substrate. Compositions described herein contain an enzyme encapsulated in a polymeric matrix containing a water-soluble polymer. The compositions also contain a substrate for the enzyme. The encapsulated enzyme may be suspended in or in the form of a sealed container surrounding a substantially non-aqueous liquid composition comprising, consisting of, or consisting essentially of the substrate, such as, for example, a liquid substrate, substrate solution, or a liquid suspension of solid substrate particles or capsules containing the substrate. Enzyme release from the polymer in which it is encapsulated is triggered by dilution into water.

DEFINITIONS

Unless defined otherwise herein, all technical and scientific terms used herein have the same meaning as commonly understood by one of ordinary skill in the art to which this invention pertains. For example, Singleton and Sainsbury, *Dictionary of Microbiology and Molecular Biology,* 2d Ed., John Wiley and Sons, NY (1994); and Hale and Marham, *The Harper Collins Dictionary of Biology*, Harper Perennial, NY (1991) provide those of skill in the art with a general dictionaries of many of the terms used in the invention. Any methods and materials similar or equivalent to those described herein find use in the practice of the present invention. Accordingly, the terms defined immediately below are more fully described by reference to the Specification as a whole. Also, as used herein, the singular terms "a," "an," and "the" include the plural reference unless the context clearly indicates otherwise. Unless otherwise indicated, nucleic acids are written left to right in 5' to 3' orientation; amino acid sequences are written left to right in amino to carboxy orientation, respectively. It is to be understood that this invention is not limited to the particular methodology, protocols, and reagents described, as these may vary, depending upon the context in which they are used by those of skill in the art.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

As used herein, the term "enzyme" refers to any protein that catalyzes a chemical reaction. The catalytic function of an enzyme constitutes its "activity" or "enzymatic activity." An enzyme typically is classified according to the type of catalytic function it carries out, e.g., hydrolysis of peptide bonds.

As used herein, the term "substrate" refers to a substance (e.g., a chemical compound) on which an enzyme performs its catalytic activity to generate a product.

As used herein, the terms "purified" and "isolated" refer to the removal of contaminants from a sample and/or to a material (e.g., a protein, nucleic acid, cell, etc.), i.e., a material that is removed from at least one component with which it is naturally associated. For example, these terms may refer to a material which is substantially or essentially free from components which normally accompany it as found in its native state, such as, for example, an intact biological system.

As used herein, the term "polynucleotide" refers to a polymeric form of nucleotides of any length and any three-dimensional structure and single- or multi-stranded (e.g., single-stranded, double-stranded, triple-helical, etc.), which contain deoxyribonucleotides, ribonucleotides, and/or analogs or modified forms of deoxyribonucleotides or ribonucleotides, including modified nucleotides or bases or their analogs. Because the genetic code is degenerate, more than one codon may be used to encode a particular amino acid, and the present invention encompasses polynucleotides which encode a particular amino acid sequence. Any type of modified nucleotide or nucleotide analog may be used, so long as the polynucleotide retains the desired functionality under conditions of use, including modifications that increase nuclease resistance (e.g., deoxy, 2'-O-Me, phosphorothioates, etc.). Labels may also be incorporated for purposes of detection or capture, for example, radioactive or nonradioactive labels or anchors, e.g., biotin. The term polynucleotide also includes peptide nucleic acids (PNA). Polynucleotides may be naturally occurring or non-naturally occurring. The terms "polynucleotide" and "nucleic acid" and "oligonucleotide" are used herein interchangeably. Polynucleotides of the invention may contain RNA, DNA, or both, and/or modified forms and/or analogs thereof. A sequence of nucleotides may be interrupted by non-nucleotide components. One or more phosphodiester linkages may be replaced by alternative linking groups. These alternative linking groups include, but are not limited to, embodiments wherein phosphate is replaced by P(O)S ("thioate"), P(S)S ("dithioate"), (O)$NR_2$ ("amidate"), P(O)R, P(O)OR', CO or $CH_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. Polynucleotides may be linear or circular or comprise a combination of linear and circular portions.

As used herein, "polypeptide" refers to any composition comprised of amino acids and recognized as a protein by those of skill in the art. The conventional one-letter or three-letter code for amino acid residues is used herein. The terms "polypeptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

As used herein, functionally and/or structurally similar proteins are considered to be "related proteins." In some embodiments, these proteins are derived from a different genus and/or species, including differences between classes of organisms (e.g., a bacterial protein and a fungal protein). In additional embodiments, related proteins are provided from the same species. Indeed, it is not intended that the processes, methods and/or compositions described herein be limited to related proteins from any particular source(s). In addition, the term "related proteins" encompasses tertiary structural homologs and primary sequence homologs. In further embodiments, the term encompasses proteins that are immunologically cross-reactive.

A "perhydrolase" refers to an enzyme that is capable of catalyzing a perhydrolysis reaction that results in the production of a sufficiently high amount of peracid suitable for use in an application such as cleaning, bleaching, disinfection, or sterilization. Generally, a perhydrolase enzyme used in methods described herein exhibits a high perhydrolysis to hydrolysis ratio. In some embodiments, the perhydrolase comprises, consists of, or consists essentially of the *Mycobacterium smegmatis* perhydrolase amino acid sequence set forth in SEQ ID NO: 1, or a variant or homolog thereof. In some embodiments, the perhydrolase enzyme comprises acyl transferase activity and catalyzes an aqueous acyl transfer reaction.

The term "perhydrolyzation" or "perhydrolyze" or "perhydrolysis" as used herein refer to a reaction wherein a peracid is generated from ester and hydrogen peroxide substrates. In one embodiment, the perhydrolyzation reaction is catalyzed with a perhydrolase, e.g., acyl transferase or aryl esterase, enzyme. In some embodiments, a peracid is produced by perhydrolysis of an ester substrate of the formula $R_1C(=O)OR_2$, where $R_1$ and $R_2$ are the same or different organic moieties, in the presence of hydrogen peroxide ($H_2O_2$). In one embodiment, —$OR_2$ is —OH. In one embodiment, —$OR_2$ is replaced by —$NH_2$. In some embodiments, a peracid is produced by perhydrolysis of a carboxylic acid or amide substrate.

The term "peracid," as used herein, refers to a molecule derived from a carboxylic acid ester which has been reacted with hydrogen peroxide to form a highly reactive product that is able to transfer one of its oxygen atoms, e.g., an organic acid of the formula $RC(=O)OOH$. It is this ability to transfer oxygen atoms that permits a peracid, for example, peracetic acid, to function as a bleaching agent.

The phrase "source of hydrogen peroxide" includes hydrogen peroxide as well as the components of a system that can spontaneously or enzymatically produce hydrogen peroxide as a reaction product.

The phrase "perhydrolysis to hydrolysis ratio" refers to the ratio of the amount of enzymatically produced peracid to the amount of enzymatically produced acid by a perhydrolase enzyme from an ester substrate under defined conditions and within a defined time.

As used herein, the term "acyl" refers to an organic group with the general formula RCO—, derived from an organic acid by removal of the —OH group. Typically, acyl group names end with the suffix "-oyl," e.g., methanoyl chloride, $CH_3CO$—Cl, is the acyl chloride formed from methanoic acid, $CH_3CO$—OH).

As used herein, the term "acylation" refers to a chemical transformation in which one of the substituents of a molecule is substituted by an acyl group, or the process of introduction of an acyl group into a molecule.

As used herein, the term "transferase" refers to an enzyme that catalyzes the transfer of a functional group from one substrate to another substrate.

As used herein, the term "enzymatic conversion" refers to the modification of a substrate or intermediate to a product, by contacting the substrate or intermediate with an enzyme. In some embodiments, contact is made by directly exposing the substrate or intermediate to the appropriate enzyme. In other embodiments, contacting comprises exposing the substrate or intermediate to an organism that expresses and/or excretes the enzyme, and/or metabolizes the desired substrate and/or intermediate to the desired intermediate and/or end-product, respectively.

As used herein, "effective amount of enzyme" refers to the quantity of enzyme necessary to achieve the activity required in the specific application (e.g., production of peracetic acid by acyl transferase for use in decontamination). Such effective amounts are readily ascertained by one of ordinary skill in the art and are based on many factors, such as the particular enzyme variant used, the specific composition, the method of decontamination, the item to be decontaminated, and the like.

As used herein, the term "stability" in reference to a substance (e.g., an enzyme) or composition refers to its ability to maintain a certain level of functional activity over a period of time under certain environmental conditions. Furthermore, the term "stability" can be used in a number of more specific contexts referring to the particular environmental condition that is of interest. For example, "thermal stability" as used herein refers to the ability of a substance or composition to maintain its function (i.e., not degrade) at increased temperature. A substantial change in stability is evidenced by at least about a 5% or greater increase or decrease (in most embodiments, it is preferably an increase) in the half-life of the functional activity being assayed, as compared to the activity present in the absence of the selected environmental conditions.

As used herein, the term "chemical stability" as used in reference to an enzyme refers to the stability of the enzyme in the presence of chemicals that adversely affect its activity. In some embodiments, such chemicals include, but are not limited to hydrogen peroxide, peracids, anionic detergents, cationic detergents, non-ionic detergents, chelants, etc. However, it is not intended that the present invention be limited to any particular chemical stability level nor range of chemical stability.

As used herein, "pH stability" refers to the ability of a substance (e.g., an enzyme) or composition to function at a particular pH. Stability at various pHs can be measured either by standard procedures known to those in the art and/or by the methods described herein. A substantial change in pH stability is evidenced by at least about 5% or greater increase or decrease (in most embodiments, it is preferably an increase) in the half-life of the functional activity, as compared to the activity at the optimum pH. It is not intended that the present invention be limited to any pH stability level nor pH range.

As used herein, "oxidative stability" refers to the ability of a substance (e.g., an enzyme) or composition to function under oxidative conditions, e.g., in the presence of an oxidizing chemical.

As used herein, "thermal stability" refers to the ability of a protein to function at a particular temperature. In general, most enzymes have a finite range of temperatures at which they will function. In addition to enzymes that work in mid-range temperatures (e.g., room temperature), there are enzymes that are capable of working in very high or very low temperatures. Thermal stability can be measured either by known procedures. A substantial change in thermal stability is evidenced by at least about 5% or greater increase or decrease in the half-life of the catalytic activity of a mutant when exposed to a different temperature (i.e., higher or lower) than optimum temperature for enzymatic activity. However, it is not intended that the processes, methods and/or compositions described herein be limited to any temperature stability level nor temperature range.

As used herein, "oxidizing chemical" refers to a chemical that has the capability of bleaching. The oxidizing chemical is present at an amount, pH and temperature suitable for bleaching. The term includes, but is not limited to hydrogen peroxide and peracids.

As used herein, the term "contaminant" refers to any substance which by its contact or association with another substance, material, or item makes it undesirable, impure, and/or unfit for use.

As used herein, the term "a contaminated item" or "item in need of decontamination" refers to any item or thing in contact or associated with a contaminant and/or which needs to be decontaminated. It is not intended that the item be limited to any particular thing or type of item. For example, in some embodiments, the item is a hard surface, while in other embodiments, the item is an article of clothing. In yet additional embodiments, the item is a textile. In yet further embodiments, the item is used in the medical and/or veterinary fields. In some embodiments, the item is a surgical instrument. In further embodiments, the item is used in transportation (e.g., roads, runways, railways, trains, cars, planes, ships, etc.). In further embodiments, the term is used in reference to food and/or feedstuffs, including but not limited to meat, meat by-products, fish, seafood, vegetables, fruits, dairy products, grains, baking products, silage, hays, forage, etc. Indeed, it is intended that the term encompass any item that is suitable for decontamination using the methods and compositions provided herein.

As used herein, the term "decontamination" refers to the removal of substantially all or all contaminants from a contaminated item. In some embodiments, decontamination encompasses disinfection, while in other embodiments, the term encompasses sterilization. However, it is not intended that the term be limited to these embodiments, as the term is intended to encompass the removal of inanimate contaminants, as well as microbial contamination. (e.g., bacterial, fungal, viral, prions, etc.).

As used herein, the term "disinfecting" refers to the removal of contaminants from the surfaces, as well as the inhibition or killing of microbes on the surfaces of items. It is not intended that the present invention be limited to any particular surface, item, or contaminant(s) or microbes to be removed.

As used herein, the term "sterilizing" refers to the killing of all microbial organisms on a surface.

As used herein, the term "sporicidal" refers to the killing of microbial spores, including but not limited to fungal and bacterial spores. The term encompasses compositions that are effective in preventing germination of spores, as well as those compositions that render spores completely non-viable.

As used herein, the terms "bactericidal," "fungicidal," and "viricidal" refer to compositions that kill bacteria, fungi, and viruses, respectively. The term "microbiocidal" refers to compositions that inhibit the growth and/or replication of any microorganisms, including but not limited to bacteria, fungi, viruses, protozoa, *rickettsia*, etc.

As used herein, the terms "bacteriostatic," "fungistatic," and "virostatic" refer to compositions that inhibit the growth and/or replication of bacteria, fungi, and viruses, respectively. The term "microbiostatic" refers to compositions that inhibit the growth and/or replication of any microorganisms, including but not limited to bacteria, fungi, viruses, protozoa, *rickettsia*, etc.

As used herein, the term "cleaning composition" refers to compositions that find use in the removal of undesired compounds from items to be cleaned, such as fabric, dishes, contact lenses, other solid substrates, hair (shampoos), skin (soaps and creams), teeth (mouthwashes, toothpastes) etc. The term further refers to any composition that is suited for cleaning, bleaching, disinfecting, and/or sterilizing any object and/or surface. It is intended that the term includes, but is not limited to detergent compositions (e.g., liquid and/or solid laundry detergents and fine fabric detergents; hard surface cleaning formulations, such as for glass, wood, ceramic and metal counter tops and windows; carpet cleaners; oven cleaners; fabric fresheners; fabric softeners; and textile and laundry pre-spotters, as well as dish detergents). The term further encompasses any materials/compounds selected for the particular type of cleaning composition desired and the form of the product (e.g., liquid, gel, granule, or spray composition), as long as the composition is compatible with the acyl transferase, hydrogen peroxide source, PGDA, and any other enzyme(s) or substance used in the composition. The specific selection of cleaning composition materials is readily made by considering the surface, item or fabric to be cleaned, and the desired form of the composition for the cleaning conditions during use. Indeed, the term "cleaning composition" as used herein, includes unless otherwise indicated, granular or powder-form all-purpose or heavy-duty washing agents, especially cleaning detergents; liquid, gel or paste-form all-purpose washing agents, especially the so-called heavy-duty liquid (HDL) types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, mouthwashes, denture cleaners, car or carpet shampoos, bathroom cleaners; hair shampoos and hair-rinses; shower gels and foam baths and metal cleaners; as well as cleaning auxiliaries such as bleach additives and "stain-stick" or pre-treat types.

As used herein, the terms "detergent composition" and "detergent formulation" are used in reference to mixtures which are intended for use in a wash medium for the cleaning of soiled objects. In some embodiments, the term is used in reference to laundering fabrics and/or garments (e.g., "laundry detergents"). In alternative embodiments, the term refers to other detergents, such as those used to clean dishes, cutlery, etc. (e.g., "dishwashing detergents"). It is not intended that the present invention be limited to any particular detergent formulation or composition. Indeed, it is intended that in addition to a perhydrolase enzyme, e.g., an acyl transferase, the term encompasses detergents that contain surfactants, transferase(s), hydrolytic enzymes, oxido reductases, builders, bleaching agents, bleach activators, bluing agents and fluorescent dyes, caking inhibitors, masking agents, enzyme activators, antioxidants, and solubilizers.

As used herein, the term "enzyme compatible," when used in the context of cleaning composition materials means that the materials do not reduce the enzymatic activity to such an extent that the relevant enzyme is not effective as desired during normal use situations.

As used herein, the term "derivative" refers to a protein which is derived from a parent protein by addition of one or more amino acids to either or both of the C- and N-terminal end(s), substitution of one or more amino acids at one or a number of different sites in the amino acid sequence, and/or deletion of one or more amino acids at either or both C- and N-terminal end(s) and/or at one or more sites in the amino acid sequence, and/or insertion of one or more amino acids at one or more sites in the amino acid sequence. The preparation of a protein derivative is often achieved by modifying a DNA sequence that encodes a native protein, transformation of the modified DNA sequence into a suitable host, and expression of the modified DNA sequence to produce the derivative protein.

Related (and derivative) proteins encompass "variant" proteins. Variant proteins differ from a parent protein and/or from one another by a small number of amino acid residues. In some embodiments, the number of different amino acid residues is any of about 1, 2, 3, 4, 5, 10, 20, 25, 30, 35, 40, 45, or 50. In some embodiments, variants differ by about 1 to about 10 amino acids.

In some embodiments, related proteins, such as variant proteins, comprise any of at least about 35%, 40%, 45%, 50%, 55%, 60%, 65%, 70%, 75%, 80%, 85%, 90%, 95%, 97%, 98%, 99%, or 99.5% amino acid sequence identity.

As used herein, the term "analogous sequence" refers to a polypeptide sequence within a protein that provides a similar function, tertiary structure, and/or conserved residues with respect to a reference protein. For example, in epitope regions that contain an alpha helix or a beta sheet structure, replacement amino acid(s) in an analogous sequence maintain the same structural element. In some embodiments, analogous sequences are provided that result in a variant enzyme exhibiting a similar or improved function with respect to the parent protein from which the variant is derived.

As used herein, "homologous protein" refers to a protein (e.g., a perhydrolase enzyme) that has similar function (e.g., enzymatic activity) and/or structure as a reference protein (e.g., a perhydrolase enzyme from a different source). Homologs may be from evolutionarily related or unrelated species. In some embodiments, a homolog has a quaternary, tertiary and/or primary structure similar to that of a reference protein, thereby potentially allowing for replacement of a segment or fragment in the reference protein with an analogous segment or fragment from the homolog, with reduced disruptiveness of structure and/or function of the reference protein in comparison with replacement of the segment or fragment with a sequence from a non-homologous protein.

As used herein, "wild-type," "native," and "naturally-occurring" proteins are those found in nature. The terms "wild-type sequence" refers to an amino acid or nucleic acid sequence that is found in nature or naturally occurring. In some embodiments, a wild-type sequence is the starting point of a protein engineering project, for example, production of variant proteins.

The term "bleaching," as used herein, means the process of treating a textile material such as a fiber, yarn, fabric, garment or non-woven material to produce a lighter color in said fiber, yarn, fabric, garment or non-woven material. For example, bleaching as used herein means the whitening of the textile by removal, modification or masking of color-causing compounds in cellulosic or other textile materials. Thus, "bleaching" refers to the treatment of a textile for a sufficient length of time and under appropriate pH and temperature conditions to effect a brightening (i.e., whitening) of the textile. Bleaching may be performed using chemical bleaching agent(s) and/or enzymatically generated bleaching agent(s). Examples of suitable bleaching agents include but are not limited to $ClO_2$, $H_2O_2$, peracids, $NO_2$, etc.

The term "bleaching agent" as used herein encompasses any moiety that is capable of bleaching a textile. A bleach activator may be required. Examples of suitable chemical bleaching agents useful in the processes, methods and compositions described herein are sodium peroxide, sodium perborate, potassium permanganate, and peracids. In some aspects, $H_2O_2$ may be considered a chemical bleaching agent when it has been generated enzymatically in situ. A "chemical bleaching composition" contains one or more chemical bleaching agent(s).

The phrase "enzymatic bleaching system" or "enzymatic bleaching composition" contains one or more enzyme(s) and substrate(s) capable of enzymatically generating a bleaching agent. For example, an enzymatic bleaching system may contain a perhydrolase enzyme, an ester substrate, and a hydrogen peroxide source, for production of a peracid bleaching agent.

An "ester substrate" in reference to an enzymatic bleaching system containing a perhydrolase enzyme refers to a perhydrolase substrate that contains an ester linkage. Esters comprising aliphatic and/or aromatic carboxylic acids and alcohols may be utilized as substrates with perhydrolase enzymes. In some embodiments, the ester source is an acetate ester. In some embodiments, the ester source is selected from one or more of propylene glycol diacetate, ethylene glycol diacetate, triacetin, ethyl acetate and tributyrin. In some embodiments, the ester source is selected from the esters of one or more of the following acids: formic acid, acetic acid, propionic acid, butyric acid, valeric acid, caproic acid, caprylic acid, nonanoic acid, decanoic acid, dodecanoic acid, myristic acid, palmitic acid, stearic acid, and oleic acid.

The term "hydrogen peroxide source" means hydrogen peroxide that is added to a textile treatment bath either from an exogenous (i.e., an external or outside) source or generated in situ by the action of a hydrogen peroxide generating oxidase on a substrate. "Hydrogen peroxide source" includes hydrogen peroxide as well as the components of a system that can spontaneously or enzymatically produce hydrogen peroxide as a reaction product.

The term "hydrogen peroxide generating oxidase" means an enzyme that catalyzes an oxidation/reduction reaction involving molecular oxygen ($O_2$) as the electron acceptor. In such a reaction, oxygen is reduced to water ($H_2O$) or hydrogen peroxide ($H_2O_2$). An oxidase suitable for use herein is an oxidase that generates hydrogen peroxide (as opposed to water) on its substrate. An example of a hydrogen peroxide generating oxidase and its substrate suitable for use herein is glucose oxidase and glucose. Other oxidase enzymes that may be used for generation of hydrogen peroxide include alcohol oxidase, ethylene glycol oxidase, glycerol oxidase, amino acid oxidase, etc. In some embodiments, the hydrogen peroxide generating oxidase is a carbohydrate oxidase.

As used herein, "textile" refers to fibers, yarns, fabrics, garments, and non-wovens. The term encompasses textiles made from natural, synthetic (e.g., manufactured), and various natural and synthetic blends. Thus, the term "textile(s)" refers to unprocessed and processed fibers, yarns, woven or knit fabrics, non-wovens, and garments. In some embodiments, a textile contains cellulose.

The term "textile(s) in need of processing" refers to textiles that need to be desized, scoured, bleached, and/or dyed or may be in need of other treatments such as biopolishing, biostonewashing, and/or softening.

The term "textile(s) in need of bleaching" refers to textiles that need to be bleached without reference to other possible treatments. These textiles may or may not have been already subjected to other treatments. Similarly, these textiles may or may not need subsequent treatments.

"Fabric" refers to a manufactured assembly of fibers and/or yarns that has substantial surface area in relation to its thickness and sufficient cohesion to give the assembly useful mechanical strength.

As used herein, the terms "purified" and "isolated" refer to the removal of contaminants from a sample and/or to a material (e.g., a protein, nucleic acid, cell, etc.) that is removed from at least one component with which it is naturally associated. For example, these terms may refer to a material which is substantially or essentially free from components which normally accompany it as found in its native state, such as, for The terms "size" or "sizing" refer to compounds used in the textile industry to improve weaving performance by increasing the abrasion resistance and strength of the yarn. Size is usually made of, for example, starch or starch-like compounds.

The terms "desize" or "desizing," as used herein, refer to the process of eliminating size, generally starch, from textiles usually prior to applying special finishes, dyes or bleaches.

"Desizing enzyme(s)" as used herein refer to enzymes that are used to enzymatically remove the size. Exemplary enzymes are amylases, cellulases and mannanases.

The term "scouring," as used herein, means to remove impurities, for example, much of the non-cellulosic compounds (e.g., pectins, proteins, wax, motes, etc.) naturally found in cotton or other textiles. In addition to the natural non-cellulosic impurities, scouring can remove, in some embodiments, residual materials introduced by manufacturing processes, such as spinning, coning or slashing lubricants. In some embodiments, bleaching may be employed to remove impurities from textiles.

The term "bioscouring enzyme(s)" refers to an enzyme(s) capable of removing at least a portion of the impurities found in cotton or other textiles.

The term "motes" refers to unwanted impurities, such as cotton seed fragments, leaves, stems and other plant parts, which cling to the fiber even after mechanical ginning process.

The term "greige" (pronounced gray) textiles, as used herein, refer to textiles that have not received any bleaching, dyeing or finishing treatment after being produced. For example, any woven or knit fabric off the loom that has not yet been finished (desized, scoured, etc.), bleached, or dyed is termed a greige textile.

The term "dyeing," as used herein, refers to applying a color, especially by soaking in a coloring solution, to, for example, textiles.

The term "non-cotton cellulosic" fiber, yarn or fabric means fibers, yarns or fabrics which are comprised primarily of a cellulose based composition other than cotton. Examples of such compositions include linen, ramie, jute, flax, rayon, lyocell, cellulose acetate and other similar compositions which are derived from non-cotton cellulosics.

The term "pectate lyase," as used herein, refers to a type of pectinase. "Pectinase" denotes a pectinase enzyme defined according to the art where pectinases are a group of enzymes that cleave glycosidic linkages of pectic substances mainly poly(1,4-alpha-D-galacturonide) and its derivatives (see Sakai et al. (1993) *Advances in Applied Microbiology* 39:213-294). Preferably, a pectinase useful herein is a pectinase enzyme which catalyzes the random cleavage of alpha-1,4-glycosidic linkages in pectic acid also called polygalacturonic acid by transelimination, such as the enzyme class polygalacturonate lyase (EC 4.2.2.2) (PGL), also known as poly(1,4-alpha-D-galacturonide) lyase, also known as pectate lyase.

The term "pectin" denotes pectate, polygalacturonic acid and pectin which may be esterified to a higher or lower degree.

The term "cutinase," as used herein, refers to as a plant, bacterial or fungal derived enzyme used in textile processing. Cutinases are lipolytic enzymes capable of hydrolyzing the substrate cutin. Cutinases can breakdown fatty acid esters and other oil-based compositions need to be removed in the processing (e.g., the scouring) of textiles. "Cutinase" means an enzyme that has significant plant cutin hydrolysis activity. Specifically, a cutinase will have hydrolytic activity on the biopolyester polymer cutin found on the leaves of plants. Suitable cutinases may be isolated from many different plant, fungal and bacterial sources.

The term "$\alpha$-amylase," as used herein, refers to an enzyme that cleaves the $\alpha$ (1-4)glycosidic linkages of amylose to yield maltose molecules (disaccharides of $\alpha$-glucose). Amylases are digestive enzymes found in saliva and are also produced by many plants. Amylases break down long-chain carbohydrates (such as starch) into smaller units. An "oxidative stable" $\alpha$-amylase is an $\alpha$-amylase that is resistive to degradation by oxidative means, when compared to non-oxidative stable $\alpha$-amylase, especially when compared to the non-oxidative stable $\alpha$-amylase form which the oxidative stable $\alpha$-amylase was derived.

The term "protease" means a protein or polypeptide domain of a protein or polypeptide derived from a microorganism, e.g., a fungus, bacterium, or from a plant or animal, and that has the ability to catalyze cleavage of peptide bonds at one or more of various positions of a protein carbohydrate backbone.

As used herein, "personal care products" means products used in the cleaning, bleaching and/or disinfecting of hair, skin, scalp, and teeth, including, but not limited to shampoos, body lotions, shower gels, topical moisturizers, toothpaste, and/or other topical cleansers. In some embodiments, these products are utilized on humans, while in other embodiments, these products find use with non-human animals (e.g., in veterinary applications).

A "suspension" or "dispersion" as used herein refers to a two phase system wherein a discontinuous solid phase is dispersed within a continuous liquid phase.

A "suspension aid" as used herein refers to a material added to a liquid composition to prevent or reduce sedimentation or floating of suspended particles. Suspension aids typically work by increasing either the viscosity or the yield stress of a carrier liquid. Fluids with a significant yield stress will flow only when stress is applied which is greater than the yield stress, and thus exhibit shear-thinning or thixotropic behavior. Effective suspension agents typically act by forming a reversible network of particles or fibers bridged by weak forces. Examples of suspending agents include, but are not limited to, xanthan gum and microfibrous cellulose, e.g., CELLULON® (CP Kelco, San Diego, Calif.).

"Encapsulated" as used herein refers to a substance that is contained within a surrounding material. This can include core/shell or matrix morphologies as described in the art (see, e.g., "Microencapsulation" Kirk-Othmer Encyclopedia of Chemical Technology, 2005).

"Miscible" as used herein refers to a liquid that is capable of mixing with another liquid, at a specified ratio of the two liquids, without separation into phases.

"Matrix" as used herein refers to a material in which a substance is enclosed or embedded.

As used herein, a "biofilm" is a collection of microorganisms embedded in a matrix of extracellular polymeric substances and various organic and inorganic compounds. Although some biofilms may contain a single species of microorganism, typically biofilms comprise not only different species of microorganisms but different types of microorganisms, for example algae, protozoa, bacteria and others.

Enzyme/Substrate Co-Delivery Systems

The invention provides a liquid delivery system for co-formulated enzyme and substrate in which at least one enzyme is encapsulated in a polymeric matrix and is formulated with a substrate for the enzyme. The substrate is in a substantially non-aqueous liquid phase in contact with the polymeric matrix and in which the polymeric matrix is not soluble. The polymeric matrix containing the enzyme may be suspended in or surround the liquid phase containing the substrate. The enzyme and substrate are not in contact in the delivery system in a configuration in which enzymatic catalysis can occur. When contacted with water, in which the polymeric matrix is soluble and in which the enzyme is catalytically active toward the substrate, catalytic activity occurs. One or multiple enzymes may be included in the composition, with at least one enzyme encapsulated in a polymeric matrix. In some embodiments, the delivery system contains two or more enzymes, encapsulated in the same polymeric matrix or in separate polymeric matrices, and the delivery system contains a substrate for at least one of the enzymes.

The substrate is solubilized or suspended in a carrier liquid that is substantially non-aqueous and in which the polymeric matrix is not soluble. The carrier liquid and polymer are chosen such that the polymeric matrix remains in a solid form and without swelling during storage. This may be achieved, for example, with low water content, reversible cross-linking, and/or low storage temperature. In some embodiments, the liquid phase contains less than about 5%, less than about 1%, or less than about 0.5% water, for example, about 4%, 3%, 2%, 1%, 0.9%, 0.8%, 0.7%, 0.6%, 0.5%, 0.4%, 0.3%, 0.2%, or 0.1% water.

The encapsulated enzyme substantially does not react with substrate in the liquid phase during storage of the delivery system. In some embodiments, less than about 20%, 10%, 5%, 1%, or 0.5% of substrate in the liquid phase is converted to product during storage for at least about 10 days, 2 weeks, 1 month, 2 months, 3 months, or longer at about 25° C. In some embodiments, less than about 20%, 10%, 5%, 1%, or 0.5% of substrate in the liquid phase is converted to product during storage for at least about 10 days, 2 weeks, 1 month, 2 months, 3 months, or longer at about 37° C. In some embodiments, less than about 20%, 10%, 5%, 1%, or 0.5% of substrate in the liquid phase is converted to product during storage for at least about 10 days, 2 weeks, 1 month, 2 months, 3 months, or longer at about 50° C.

In a delivery system as described herein, an encapsulated enzyme retains at least about 50%, 60%, 70%, 80%, 90%, 91%, 92%, 93%, 94%, 95%, 96%, 97%, 98%, 99%, or essentially all of the initial catalytic potential in the polymeric matrix, releasable upon contact with water, but substantially does not react with the substrate in the composition for at least about 10 days, 2 weeks, 1 month, 2 months, 3 months, or longer at 25° C., 37° C., or 50° C.

Polymeric Matrix

The polymeric matrix comprises, consists of, or consists essentially of a polymer that is insoluble in a carrier fluid containing the substrate and soluble in water. In some embodiments, the polymeric matrix comprises, consists of, or consists essentially of polyvinyl alcohol, methylcellulose, hydroxypropyl methylcellulose, polyvinyl pyrrolidone, guar gum, or a derivative or co-polymer thereof, or a mixture thereof. In some embodiments, the polymeric matrix contains one or more filler or extender (e.g., starch, sugar, clay, talc, calcium carbonate, titanium dioxide, cellulose fibers), plasticizer (e.g., glycerol, sorbitol, propylene glycol), cosolvent, binder, swelling agent (e.g., polyacrylate, croscarmellose sodium, sodium starch glycolate, low-substituted hydroxypropyl cellulose, galactomannan, Water-Lok, ZapLoc), or release agent.

In some embodiments, the polymers are negatively-charged polymers, such as hetero-polysaccharides including glucuronide and/or galacturonide residues. Such polysaccharides may for example include material produced by the organisms from which the enzymes themselves have been produced, and may remain as contaminants in the partially purified enzyme preparations even though they do not have, themselves have useful enzymatic activity. Alternatively or additionally, such polysaccharides may be added separately, in amounts up to about 1 to 5% by weight or more of the slurry. Such amounts may be comparable with those of the enzymes themselves. In some embodiments, the polysaccharides are present (or added) before spray-drying. Other exemplary polymers are arabinogalactans, xylogalalctans, and, generally, acid polysaccharides.

In some embodiments, the polymeric matrix includes proteins, peptides, or derivatives, thereof. Some or all of the proteins or peptides may be present in a fermentation broth, cell media, or partially-purified protein preparations, and may remain as contaminants in the partially purified enzyme preparations even though they do not have, themselves have useful enzymatic activity. Alternatively or additionally, such polysaccharides may be added separately, in amounts up to about 1 to 5% by weight or more of the slurry. Such amounts may be comparable with those of the enzymes themselves.

In various embodiments, enzymes (and optionally substrates) are encapsulated in polymers using techniques including, but not limited to, solvent casting, spray drying, lyophilization/freeze-drying, fluid bed spray-coating, fluid-bed agglomeration, spray chilling, wet granulation, drum granulation, high-shear granulation, extrusion, pan coating, coacervation, gelation, and atomization. In particular embodiments, spray-drying is used.

Generally, the amount of enzyme encapsulated in the polymeric matrix is less than 50% by weight. In various embodiments, the amount of enzyme encapsulated in the polymeric matrix is about 0.01% to about 50%, about 0.1% to about 25%, about 1% to about 10%, or about 2% to about 5% by weight.

In some embodiments, the enzyme-containing polymeric matrix is in the form of particles that are suspended in a liquid phase containing the substrate. In various embodiments, the particles are about 0.1 to about 1000, about 50 to about 250, about 100 to about 300, about 200 to about 500, about 400 to about 800, or about 600 to about 1000 micrometers in diameter.

In some embodiments, the polymeric matrix is in the form of a film which is about 5 to about 1000, about 50 to about 100, about 100 to about 200, or about 200 to about 500, or about 500 to about 1000 micrometers in thickness.

In some embodiment, the enzyme-containing polymeric matrix is in the form of a film forming a sealed container (e.g., a pouch, sachet, or capsule) surrounding a liquid phase that contains the substrate.

Enzymes

In various embodiments, the delivery system contains one or more proteases, esterases, serine hydrolases, lipases, perhydrolases, oxidases, phenol oxidizing enzymes, laccases, acyl transferases, aryl esterases, perhydrolases, amylases, pectinases, xylanases, cellulases, hemicellulases, catalases, peroxidases, carbohydrates oxidase, mannanases, phytases, pectinases, peroxidases, carbohydrate oxidases, cutinases, catalases, or a mixture, thereof.

In one embodiment, the delivery system contains a laccase (a multi-copper oxidase, EC 1.10.3.2, for example, from *Cerrena unicolor*) and a mediator (substrate) for the laccase, such as 2,2'-azino-bis(3-ethylbenzothiazoline-6-sulfonic acid) diammonium salt (ABTS), syringonitrile (SN), syringamide (SA), methyl syringate (MS), or 10-carboxypropyl phenothiazine (PTP), or a mediator as described in European Patent No. 1 064 359, 1 141 321, or 0 805 465, U.S. Pat. No. 6,329,332, PCT Application No. 00/05349, or U.S. Publication No. 2008/0196173.

In one embodiment, the laccase enzyme comprises, consists of, or consists essentially of, the amino acid sequence depicted in SEQ ID NO: 1, below, or a variant or homologue, thereof, having at least 70, 75, 80, 85, 86, 87, 88, 89, 90, 91, 92, 93, 94, 95, 96, 97, 98, or even 99% or more sequence identity, or an amino acid sequence as described in PCT Application No. WO2008/076322, or a variant or homologue thereof having at least 70, 75, 80, 85, 90, 91, 92, 93, 94, 95, 96, 97, 98, or 99, or even 99.5% or more sequence identity.

```
                                         (SEQ ID NO: 1)
AIGPVADLHIVNKDLAPDGVQRPTVLAGGTFPGTLITGQKGDNFQLNV

IDDLTDDRMLTPTSIHWHGFFQKGTAWADGPAFVTQCPIIADNSFLYD

FDVPDQAGTFWYHSHLSTQYCDGLRGAFVVYDPNDPHKDLYDVDDGGT

VITLADWYHVLAQTVVGAATPDSTLINGLGRSQTGPADAELAVISVEH

NKRYRFRLVSISCDPNFTFSVDGHNMTVIEVDGVNTRPLTVDSIQIFA

GQRYSFVLNANQPEDNYWIRAMPNIGRNTTTLDGKNAAILRYKNASVE

EPKTVGGPAQSPLNEADLRPLVPAPVPGNAVPGGADINHRLNLTFSNG

LFSINNASFTNPSVPALLQILSGAQNAQDLLPTGSYIGLELGKVVELV

IPPLAVGGPHPFHLHGHNFWVVRSAGSDEYNFDDAILRDVVSIGAGTD

EVTIRFVTDNPGPWFLHCHIDWHLEAGLAIVFAEGINQTAAANPTPQA

WDELCPKYNGLSASQKVKPKKGTAI.
```

In some embodiments, the delivery system contains a perhydrolase enzyme (e.g., acyl transferase; aryl esterase) and substrate(s) for producing a peracid for example, an acyl donor such as an ester substrate, e.g, propylene glycol diacetate (PGDA), and a hydrogen peroxide source, e.g., sodium percarbonate, sodium perborate, urea hydrogen peroxide, or an enzymatic hydrogen peroxide generating system, for example, a hydrogen peroxide generating oxidase and its substrate, e.g., glucose oxidase and glucose.

In some embodiments, the perhydrolase enzyme is a naturally occurring *M. smegmatis* perhydrolase enzyme. In some embodiments, the perhydrolase enzyme comprises, consists of, or consists essentially of the amino acid sequence set forth in SEQ ID NO: 2 or a variant or homologue thereof. In some embodiments, the perhydrolase enzyme comprises, consists of, or consists essentially of an amino acid sequence that is at least about 80%, 85%, 90%, 91%, 92%, 93%, 94%, 95%, 96%, 97%, 98%, 99%, or even 99.5%, or more, identical to the amino acid sequence set forth in SEQ ID NO: 2.

The amino acid sequence of *M. smegmatis* perhydrolase is shown below:

```
                                         (SEQ ID NO: 2)
MAKRILCFGDSLTWGWVPVEDGAPTERFAPDVRWTGVLAQQLGADFEV

IEEGLSARTTNIDDPTDPRLNGASYLPSCLATHLPLDLVIIMLGTNDT

KAYFRRTPLDIALGMSVLVTQVLTSAGGVGTTYPAPKVLVVSPPPLAP

MPHPWFQLIFEGGEQKTTELARVYSALASFMKVPFFDAGSVISTDGVD

GIHFTEANNRDLGVALAEQVRSLL
```

The corresponding polynucleotide sequence encoding *M. smegmatis* perhydrolase is (5'-3'):

```
                                         (SEQ ID NO: 3)
ATGGCCAAGCGAATTCTGTGTTTCGGTGATTCCCTGACCTGGGGCTGG

GTCCCCGTCGAAGACGGGGCACCCACCGAGCGGTTCGCCCCCGACGTG

CGCTGGACCGGTGTGCTGGCCCAGCAGCTCGGAGCGGACTTCGAGGTG

ATCGAGGAGGGACTGAGCGCGCGCACCACCAACATCGACGACCCCACC

GATCCGCGGCTCAACGGCGCGAGCTACCTGCCGTCGTGCCTCGCGACG

CACCTGCCGCTCGACCTGGTGATCATCATGCTGGGCACCAACGACACC

AAGGCCTACTTCCGGCGCACCCCGCTCGACATCGCGCTGGGCATGTCG

GTGCTCGTCACGCAGGTGCTCACCAGCGCGGGCGGCGTCGGCACCACG

TACCCGGCACCCAAGGTGCTGGTGGTCTCGCCGCCACCGCTGGCGCCC

ATGCCGCACCCCTGGTTCCAGTTGATCTTCGAGGGCGGCGAGCAGAAG

ACCACTGAGCTCGCCCGCGTGTACAGCGCGCTCGCGTCGTTCATGAAG

GTGCCGTTCTTCGACGCGGGTTCGGTGATCAGCACCGACGGCGTCGAC

GGAATCCACTTCACCGAGGCCAACAATCGCGATCTCGGGGTGGCCCTC

GCGGAACAGGTGCGGAGCCTGCTGTAA-3'.
```

In some embodiments, the perhydrolase enzyme comprises one or more substitutions at one or more amino acid positions equivalent to position(s) in the *M. smegmatis* perhydrolase amino acid sequence set forth in SEQ ID NO: 2. In some embodiments, the perhydrolase enzyme comprises any one or any combination of substitutions of amino acids selected from M1, K3, R4, I5, L6, C7, D10, S11, L12, T13, W14, W16, G15, V17, P18, V19, D21, G22, A23, P24, T25, E26, R27, F28, A29, P30, D31, V32, R33, W34, T35, G36, L38, Q40, Q41, D45, L42, G43, A44, F46, E47, V48, I49, E50, E51, G52, L53, S54, A55, R56, T57, T58, N59, I60, D61, D62, P63, T64, D65, P66, R67, L68, N69, G70, A71, S72, Y73, S76, C77, L78, A79, T80, L82, P83, L84, D85, L86, V87, N94, D95, T96, K97, Y99F100, R101, R102, P104, L105, D106, I107, A108, L109, G110, M111, S112, V113, L114, V115, T116, Q117, V118, L119, T120, S121, A122, G124, V125, G126, T127, T128, Y129, P146, P148, W149, F150, I153, F154, I194, and F196.

In some embodiments, the perhydrolase enzyme comprises one or more of the following substitutions at one or more amino acid positions equivalent to position(s) in the *M. smegmatis* perhydrolase amino acid sequence set forth in SEQ ID NO: 2: L12C, Q, or G; T25S, G, or P; L53H, Q, G, or S; S54V, L A, P, T, or R; A55G or T; R67T, Q, N, G, E, L, or F; K97R; V125S, G, R, A, or P; F154Y; F196G.

In some embodiments, the perhydrolase enzyme comprises a combination of amino acid substitutions at amino acid positions equivalent to amino acid positions in the *M. smegmatis* perhydrolase amino acid sequence set forth in SEQ ID NO:2: L12I+S54V; L12M+S54T; L12T+S54V; L12Q+T25S+S54V; L53H+ S54V; S54P+V125R; S54V+ V125G; S54V+F196G; S54V+K97R+V125G; or A55G+ R67T+K97R+V125G.

In some embodiments, the liquid suspension contains a perhydrolase enzyme and substrates for producing mono- and diglycerides (e.g., an acyl donor and alcohol acceptor) or a sorbitan ester (e.g., an acyl donor and sorbitan). In some embodiments, the liquid suspension contains a perhydrolase enzyme and substrates for producing a fragrant ester, for example, a benzyl ester (e.g., an acyl donor and a volatile alcohol, for example benzyl alcohol).

In some embodiments, the enzyme is a perhydrolase and the delivery system contains an ester substrate or ester substrate mixture, for example, an acetate ester, e.g., propylene glycol diacetate (PGDA), ethyl acetate, butyl acetate, hexyl acetate, octyl acetate, ethyl propionate, butyl propionate, hexyl propionate, isoamyl acetate, citronellyl acetate, citronellyl propionate, dodecyl acetate, Neodol 23-3 acetate, Neodol 23-9 acetate, ethylene glycol diacetate, triacetin, tributyrin, ethyl methoxyacetate, linalyl acetate, ethyl butyrate, ethyl isobutyrate, ethyl-2-methyl butyrate, ethyl isovalerate, diethyl isovalerate, diethyl maleate, ethyl glycolate, or a mixture thereof.

In some embodiments, the delivery system contains a protease and at least one other protease-sensitive enzyme, i.e., an enzyme that is hydrolysable by the protease, encapsulated in the same or separate polymeric matrices, or wherein one of the protease or the protease-sensitive enzyme is encapsulated in a polymeric matrix and the other enzyme is in a liquid phase in the delivery system, and the protease is substantially not catalytically active toward the protease-sensitive enzyme until water is added to the delivery system.

Carrier Liquids

The delivery system includes a substrate for an encapsulated enzyme in a carrier liquid in which the polymeric matrix (in which the enzyme is encapsulated) is substantially insoluble. Nonlimiting examples of carrier liquids include glycols, nonionic surfactants, alcohols, polyglycols, and acetate esters. In some embodiments, the carrier liquid is, itself, a substrate for the enzyme.

Optional Adjunct Ingredients

In some embodiments, the delivery system includes one or more surfactants, i.e., a nonionic, anionic, cationic, ampholytic, zwitterionic, or semi-polar nonionic surfactant, or a mixture, thereof. In some embodiments, the delivery system includes one or more of: a suspension aid, a chelating agent, a stabilizing agent, an emulsifier, a buffering agent, and/or a mixture thereof.

Compositions

The invention provides compositions containing enzyme/substrate co-delivery systems as described herein. Exemplary compositions include: a cleaning composition, a disinfecting composition, a decontamination composition, a textile processing composition, a bleaching composition, a textile dyeing composition, a personal care composition, a hair dyeing composition, a pulp or paper processing composition, a wood composite producing composition, a waste water processing composition, a baking composition, a brewing composition, an animal feed composition, a starch processing composition, and/or an ethanol fermenting composition. The delivery system may be stored in the composition or may be mixed into the composition at the point of use.

In one embodiment, a detergent composition is provided for use in a cleaning application. In addition to the enzyme/substrate co-delivery system described herein, a detergent composition may contain one or more detergent ingredients selected from surfactants, builders, bleaches, bleach precursors, enzyme stabilizers, complexing agents, chelating agents, foam regulators, corrosion inhibitors, anti-electrostatic agents, dyes, perfumes, bactericides, fungicides, and activators. The delivery system may be stored in the detergent composition or may be mixed into the composition at the point of use.

Methods of Use

Cleaning Methods

The enzyme/substrate co-delivery systems described herein may be used in methods for cleaning. In some embodiments, the invention provides a method for cleaning, comprising contacting an article containing a stain with a detergent composition comprising an enzyme/substrate co-delivery system as described herein in the presence of water, wherein at least a portion of the stain is removed. Enzymes suitable for use in cleaning methods herein include, but are not limited to, proteases, amylases, perhydrolases, oxidases, lipases, cellulases, xylanases, mannanases, esterases, cutinases, polyesterases, pectinases, phenol oxidizing enzymes, catalases, lysozymes, and hemicellulases.

In one embodiment, the invention provides a method for inhibiting transfer of dye from a dyed fabric to another fabric during washing, comprising an enzyme/substrate co-delivery system as described herein in the presence of water, wherein the delivery system contains an enzyme capable of bleaching, for example, a phenol oxidizing enzyme, such as a laccase, or a peroxidase, wherein at least a portion of colored substances leached from dyed and/or soiled fabric are bleached, thereby preventing redeposition of the colored substances to the other fabric in the wash.

Textile Processing Methods

The enzyme/substrate co-delivery systems described herein may be used in methods for textile processing. In some embodiments, the invention provides a method for bleaching of a textile, comprising contacting a textile with an enzyme/substrate co-delivery system containing at least one enzyme and substrate capable of bleaching a textile, for example, a perhydrolase and substrates for producing a peracid or a phenol oxidizing enzyme, e.g., a laccase, and a mediator capable of producing a bleaching effect, in the presence of water, for a length of time and under conditions suitable to permit measurable whitening of the textile, thereby producing a bleached textile. In some embodiments, the invention provides a method for changing the color of a textile (e.g., dyeing the textile), comprising contacting a textile with an enzyme/substrate co-delivery system containing an enzyme and substrate capable of changing the color of a textile, for example, a phenol oxidizing enzyme, e.g., a laccase, and a mediator capable of effecting a color change, in the presence of water, for a length of time and under conditions suitable to permit a measurable change of color in the textile, thereby producing a textile with a change in color.

In some embodiments, the invention provides methods for combined pretreatment of textiles in a single process, wherein the enzyme/substrate co-delivery system comprises at least two textile processing enzymes. For example, a combined process for desizing, scouring, and bleaching includes a perhydrolase enzyme and substrate(s) (e.g., ester substrate and hydrogen peroxide source) as described herein and amylase and pectinase enzymes. A combined scouring and bleaching process includes a perhydrolase enzyme and substrate(s) as described herein and a pectinase enzyme. A combined desizing and bleaching process includes a perhydrolase enzyme and substrate(s) as described herein and an amylase enzyme. A pectinase enzyme in the combined textile pretreatment methods described herein may be used by itself or in combination with one or more other enzymes such as protease, lipase, cellulase, cutinase, and/or hemicellulase.

Sanitizing, Disinfecting and/or Decontaminating Methods Using a Perhydrolase Enzyme The enzyme/substrate co-delivery systems of the present invention (and related systems and kits incorporating these compositions) can be used in a range of methods for decontaminating, disinfecting, and/or sanitizing items.

In some embodiments, the method for decontamination comprises: (a) providing an enzyme/substrate co-delivery system as described herein comprising an enzyme with perhydrolase activity encapsulated in a water-soluble polymer, wherein said activity comprises a perhydrolysis to hydrolysis ratio of at least 2:1; a hydrogen peroxide source; and an ester substrate; and (b) adding the composition to water and mixing under conditions and for a length of time sufficient to solubilize the polymeric matrix and to generate an aqueous solution of at least about 0.16% peracetic acid by weight, e.g., at least about 20 minutes, and a pH less than about 9.0; and (c) exposing an item comprising a contaminant to the solution.

In one embodiment, the method for decontamination comprises: (a) providing an enzyme/substrate co-delivery system comprising an acyl transferase enzyme encapsulated in a water-soluble polymer, a hydrogen peroxide source, and propylene glycol diacetate; (b) adding the composition to water and mixing under conditions and for a length of time sufficient to solubilize the polymeric matrix and to generate an aqueous solution of at least about 0.16% peracetic acid by weight, e.g., at least about 20 minutes; and (c) exposing an item comprising a contaminant to said solution.

In some embodiments, the hydrogen peroxide source is a hydrogen peroxide generating compound, for example, selected from sodium percarbonate, sodium perborate, and urea hydrogen peroxide. In some embodiments, the hydrogen peroxide source is an enzymatic system, such as a hydrogen peroxide generating oxidase and its substrate, e.g., glucose oxidase and glucose. The hydrogen peroxide generating oxidase may be encapsulated in a polymeric matrix (the same as or separate from the polymeric matrix in which the perhydrolase enzyme is encapsulated) or solubilized or suspended in the liquid phase in the delivery system. The substrate for the hydrogen peroxide generating oxidase may be encapsulated in a polymeric matrix (the same as or separate from the polymeric matrix in which the perhydrolase enzyme is encapsulated) or solubilized or suspended in the liquid phase in the delivery system.

Depending on the specific type of contaminant to be removed, the step of exposing the item to the peracid solution may be performed over a wide range of time scales. For example, in certain sanitizing procedures exposure times as short as about 30 seconds, 1 minute, 5 minutes or 10 minutes may be sufficient. However, in other applications (e.g., removal of biofilms), it may be necessary to expose the item for considerably longer periods of time, such as about 30 minutes, 1 hour, 6 hours, 12 hours, 24 hours, or even longer, in order to achieve adequate level of decontamination.

Similarly, the temperature of the peracid solution during the exposure step may be adjusted depending on the particular type of contaminant. In one embodiment, the exposure temperature is the ambient temperature at which the solution is prepared, i.e., typically about 18-25° C. In other embodiments, higher temperatures may be used to facilitate the decontamination process. Generally, higher temperatures will accelerate the reactivity of the peracid solution, thereby accelerating the decontamination process. Thus, in some embodiments, the exposure step may be carried out with the peracid solution at about 30° C., 37° C., 45° C., 50° C., 60° C., 75° C., 90° C., or even higher.

In one embodiment of the methods, the enzyme-containing polymeric matrix is in the form of a water soluble container in which the substrates are enclosed in a liquid phase and the container is added to the water.

The methods of decontamination are useful against a wide range of contaminants including toxins selected from the group consisting of botulinum toxin, anthracis toxin, ricin, scombroid toxin, ciguatoxin, tetrodotoxin, mycotoxins, and any combination thereof; and pathogens selected from the group consisting of bacteria, viruses, fungi, parasites, prions, and any combination thereof. For example, the methods disclosed herein may be used for decontamination of materials contaminated with materials including but not limited to toxic chemicals, mustard, VX, *B. anthracis* spores, *Y. pestis, F. tularensis*, fungi, and toxins (e.g., botulinum, ricin, mycotoxins, etc.), as well as cells infected with infective virions (e.g., flaviviruses, orthomyxoviruses, paramyxoviruses, arenaviruses, rhabdoviruses, arboviruses, enteroviruses, bunyaviruses, etc.). In some embodiments, the at least one pathogen is selected from *Bacillus* spp., *B. anthracis, Clostridium* spp., *C. botulinum, C. perfringens, Listeria* spp., *Pseudomonas* spp., *Staphylococcus* spp., *Streptococcus* spp., *Salmonella* spp., *Shigella* spp., *E. coli, Yersinia* spp., *Y. pestis, Francisella* spp., *F. tularensis, Camplyobacter* ssp., *Vibrio* spp., *Brucella* spp., *Cryptosporidium* spp., *Giardia* spp., *Cyclospora* spp., and *Trichinella* spp.

The peracid solutions generated using the delivery systems described herein and the methods of their use are effective at decontaminating biofilms. One of the characterizing features of biofilms is that the microorganisms therein act cooperatively or synergistically. Empirically it has been found that microorganisms living in a biofilm are better protected from biocides than microorganisms living outside a biofilm. Thus, removal of pathogenic biofilms represents a particularly difficult problem in decontaminating and/or sanitizing equipment.

In some embodiments, the stable compositions made be used to generate a peracid solution are useful to remove biofilms, including those formed by one or more pathogenic bacteria selected from the group consisting of: *Bacillus* spp., *B. anthracis, Clostridium* spp., *C. botulinum, C. perfringens, Listeria* spp., *Pseudomonas* spp., *Staphylococcus* spp., *Streptococcus* spp., *Salmonella* spp., *Shigella* ssp., *E. coli, Yersinia* spp., *Y. pestis, Francisella* spp., *F. tularensis, Camplyobacter* ssp., *Vibrio* spp., *Brucella* spp., *Cryptosporidium* spp., *Giardia* spp., *Cyclospora* spp., *Trichinella* spp., and any combination thereof. In one embodiment, a peracid solution made by the methods of the present invention may be used to decontaminate biofilms selected from group consisting of: *Pseudomonas aeruginosa, Staphylococcus aureus* (SRWC-10943), *Listeria monocytogenes* (ATCC 19112), and any combination thereof.

In one embodiment, pathogenic biofilms comprising bacterial cultures of *Pseudomonas* spp., *Staphylococcus* spp., and/or *Listeria* spp., contaminating stainless steel equipment can be substantially removed (i.e., ~500-1000-fold reduction) by exposure to a 0.16% by weight PAA solution (generated from the perhydrolase containing enzyme/substrate co-delivery system) at 45° C. for 45 minutes.

In various embodiments, the methods of decontamination using the perhydrolase containing delivery systems described herein are useful for sanitizing/decontaminating a wide range of contaminated items including hard surfaces, fabrics, food, feed, apparel, rugs, carpets, textiles, medical instruments, veterinary instruments, for example, stainless steel items and equipment, including large reactors, used in pharmaceutical and biotechnology processes.

The peracid solutions generated enzymatically using the delivery systems described herein are particularly well-suited for cleaning stainless steel items and equipment because the ratio of peracid to corresponding acid generated in aqueous solution is much higher than found in commercial solutions. For example, a peracetic acid (PAA) solution generated using the stable composition of S54V variant of MsAcT, percarbonate, and propylene glycol diacetate (PGDA), will have a ratio of PAA to acetic acid of approximately 10:1. Commercial PAA solutions typically have more acetic acid than PAA and may even have the reversed ratio (1:10). The increased ratio of PAA to acetic acid reduces, or completely obviates, the need to carry out further passivating treatments of the stainless steel item or equipment following the PAA treatment. Thus, in some embodiments, peracid solutions generated using the stable compositions of the present invention may be used to sanitize stainless steel items and equipment, including large reactors, used in pharmaceutical and biotechnology processes. In some embodiments, the peracid solutions may be used to sanitize stainless steel items and equipment in a single-step, without the need for any further treatment of the steel with a passivating agent.

In still further embodiments, the delivery systems described herein may be used in decontamination of food and/or feed, including but not limited to vegetables, fruits, and other food and/or feed items. Indeed, it is contemplated that the present invention will find use in the surface cleaning of fruits, vegetables, eggs, meats, etc. Indeed, it is intended that the present invention will find use in the food and/or feed industries to remove contaminants from various food and/or feed items. In some embodiments, methods for food and/or feed decontamination set forth by the Food and Drug Administration and/or other food safety entities, as known to those of skill in the art find use with the present invention.

In still further embodiments, the item in need of decontamination is selected from hard surfaces, fabrics, food, feed, apparel, rugs, carpets, textiles, medical instruments, and veterinary instruments. In some embodiments, the food is selected from fruits, vegetables, fish, seafood, and meat. In some still further embodiments, the hard surfaces are selected from household surfaces and industrial surfaces. In some embodiments, the household surfaces are selected from kitchen countertops, sinks, cupboards, cutting boards, tables, shelving, food preparation storage areas, bathroom fixtures, floors, ceilings, walls, and bedroom areas. In some alternative embodiments, the industrial surfaces are selected from food processing areas, feed processing areas, tables, shelving, floors, ceilings, walls, sinks, cutting boards, airplanes, automobiles, trains, and boats.

Kits

The invention also provides kits of parts or "kits." In one embodiment, a kit provides an enzyme/substrate co-delivery system as described herein, with instructions for use in an application, including any of the methods described herein (for example, a cleaning method or a textile processing method), in which enzyme activity upon dilution in water, is useful. Suitable packaging is provided. As used herein, "packaging" refers to a solid matrix or material customarily used in a system and capable of holding within fixed limits components of a kit as described herein, e.g., an enzyme/substrate co-delivery system.

Instructions may be provided in printed form or in the form of an electronic medium such as a floppy disc, CD, or DVD, or in the form of a website address where such instructions may be obtained.

The following examples are intended to illustrate, but not limit, the invention.

EXAMPLES

Example 1

Enzyme-containing polyvinyl alcohol (PVA) matrices were prepared using a solvent casting method. One part of liquid enzyme concentrate (about 35 mg/ml enzyme) was added to nine parts of a 10% polymer solution and mixed thoroughly. This solution was spread onto a glass sheet and allowed to dry at ambient temperature. The dried polymer films contained approximately 3.5 mass % enzyme, and had thickness of about 50-100 p.m. These films were cut into 4 mm diameter circular disks for subsequent testing.

The PVA polymers used in this experiment were two different DuPont commercial grades: Elvanol 51-05 (88% hydrolysis, 500 nominal degree of polymerization) and Elvanol 71-30 (98% hydrolysis, 1500 nominal degree of polymerization).

Enzyme Leaching

To assess leaching of enzyme, disks were incubated in propylene glycol diacetate (PGDA) for about 46 hours in glass vials at 37° C. After the incubation, the disks were removed from the glass vials and excess PGDA was removed by blotting with tissue wipes. Disks were placed in 4 ml $H_2O$ to solubilize the PVA. Enzyme activity in each pre-incubated disk was measured and compared to activity in freshly cut disks that had not been incubated in PGDA, using the pNB rate assay.

The pNB rate assay was performed as follows:

Reaction scheme:

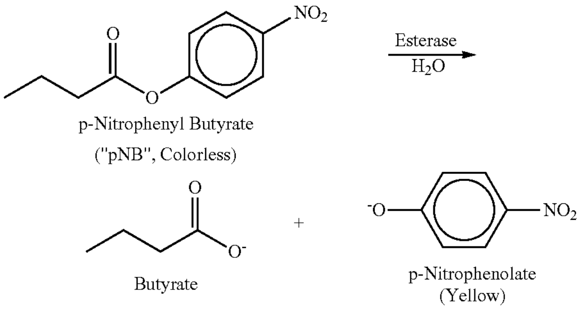

p-Nitrophenyl Butyrate ("pNB", Colorless)

Butyrate p-Nitrophenolate (Yellow)

Assay Buffer (100 mM Tris pH 8.0+0.1% Triton X-100)

To prepare 1000 mL, dilute 100 mL 1M Tris (pH 8.0) and 1.0 mL Triton X-100 into Milli-Q water.

Substrate Stock (100 mM p-Nitrophenyl Butyrate in DMSO)

To prepare 10 mL, add 174.3 μL pNB to 10 mL DMSO Divide into 1-mL aliquots and store at −20° C. A working solution can be kept at room temperature and discarded when the background yellow color becomes unacceptably high.

Single Cuvette Protocol

1. Set up spectrophotometer with standard AAPF assay program, temperature at 25° C.
2. Dilute 10 μL Substrate Stock into 1 mL Assay Buffer in a disposable 1-mL cuvette. Equilibrate at 25° C.
3. Initiate reaction with 10 μl enzyme solution
4. Start spectrophotometer.
5. Determine rate ($\Delta A_{410}$/min)

The results are shown in Table 1.

Textile Bleaching

Three each 3 in.×4 in. 100% cotton fabric swatches (Testfabrics, style #428U, desized cotton sateen) and three each 3 in.×4 in. cotton interlock swatches were washed in a Launder-O-Meter with and without PVA perhydrolase disks, under the following conditions:

Liquor ratio: 50:1 pH 7 (100 M sodium phosphate buffer)

Temperature: 60° C.

PGDA: 4 ml/l $H_2O_2$ (50%): 4 ml/l

Incubation time: 60 min

Perhydrolase enzyme: seven 5/32 in. PVA perhydrolase disks

Bleaching performance with respect to the 100% cotton sateen swatches was quantified by measuring CIE L* values using a Minolta CR-200 Chromameter. Higher CIE L* values indicate higher bleaching effects. The results are shown in Table 1. The cotton interlock was included as ballast and bleaching of interlock was not assessed.

A "no enzyme" control included all of the above components except the PVA perhydrolase disks.

TABLE 2

| Enzyme | Disk | Activity* | Std. Dev. |
|---|---|---|---|
| Perhydrolase | Control | 0.543 | 0.019 |
| | PGDA | 0.544 | 0.023 |
| Amylase | Control | 0.042 | 0.001 |
| | PGDA | 0.040 | 0.002 |

Textile Bleaching and Desizing

Three 3 in.×4 in. greige cotton sateen fabric swatches (Testfabrics, style #428R) and three 3 in.×4 in. greige cotton interlock swatches were washed in a Launder-Ometer with and without PVA perhydrolase/amylase disks, under the following conditions:

Liquor ratio: 50:1 pH: 7 (100 mM sodium phosphate buffer)

Temperature: 60° C.

PGDA: 4 ml/l $H_2O_2$ (50%): 4 ml/l

Incubation time: 60 min

Enzymes: fifteen 5/32 in. PVA perhydrolase/amylase disks

To assess desizing, 5/8 in. fabric disks were cut from each treated greige swatch, and then the disks were stained with iodine solution for 1 min at room temperature. The fabric disks were then rinsed with cold water, dabbed with wipes, and the color of the disks was then measured using a Minolta CR-200 Chromameter. CIE L* values were calculated to quantify the depth of the iodine staining. Bleaching performance was assessed for the swatches as described in Example 1. A lighter color on a fabric disk indicates that there is less starch present, indicating higher desizing efficacy. The results are shown in Table 3.

TABLE 1

| Film | | Dish weight | Rate (dissolved in 4 ml $H_2O$) | | | | Total enzyme activity/mg disk | | | Whiteness (CIE L4) | |
|---|---|---|---|---|---|---|---|---|---|---|---|
| Type | | (mg) | 1 | 2 | Ave | Stdev | | Ave | Stdev | Ave | Stdev |
| 51-05 | Fresh disk 1 | 2.0 | 0.79 | 0.75 | 0.77 | 0.03 | 1537 | 1513 | 35 | 93.44 | 0.10 |
| | Fresh disk 2 | 2.0 | 0.73 | 0.76 | 0.74 | 0.02 | 1488 | | | | |
| | Incubated disk 1 | 1.9 | 0.68 | 0.69 | 0.68 | 0.01 | 1441 | 1473 | 45 | | |
| | Incubated disk 2 | 2.0 | 0.73 | 0.78 | 0.75 | 0.03 | 1504 | | | | |
| 71-30 | Fresh disk 1 | 2.5 | 0.75 | 0.76 | 0.75 | 0.00 | 1206 | 1189 | 24 | 93.30 | 0.10 |
| | Fresh disk 2 | 2.6 | 0.76 | 0.77 | 0.76 | 0.01 | 1172 | | | | |
| | Incubated disk 1 | 2.3 | 0.72 | 0.73 | 0.73 | 0.01 | 1261 | 1220 | 57 | | |
| | Incubated disk 2 | 2.6 | 0.76 | 0.78 | 0.77 | 0.01 | 1180 | | | | |
| No Enz | | | | | | | | | | 89.33 | 0.15 |

Example 2

Circular disks 5/32 in. in diameter were cut from PVA film (Elvanol 51-05) that was about 50-100 μm in thickness and contained encapsulated perhydrolase and α-amylase enzymes ("PVA perhydrolase/α-amylase disks"). The enzymes were encapsulated in the polymeric matrix as described above, but with 9 parts 10% polymer solution to 1 part each of perhydrolase concentrate and amylase concentrate. The resulting polymer film was approximately 2.5 mass % of each enzyme.

Enzyme Leaching

To assess leaching of enzyme from the disks, three disks were incubated in sealed glass vials with or without PGDA at 37° C. for 60 hours. After removal from the vials, each disk was dissolved in 4 ml Milli-Q water. Alpha-amylase activity was measured using the Ceralpha rate assay kit available from Megazyme International Ireland Limited. Alpha-amylase activity was assessed by hydrolysis of blocked p-nitrophenyl maltoheptaoside in the presence of excess levels of a thermostable α-glucosidase, resulting in quantitative hydrolysis of the p-nitrophenyl maltosaccharide fragment to glucose and free p-nitrophenol. Perhydrolase activity was measured using the pNB rate assay as described in Example 1. The results are shown in Table 2. Perhydrolase activity (*) is the average of six measurements (two per disk) and amylase activity is the average of three measurements (one per disk). Activity is represented as $\Delta A_{410}$/min for both enzymes.

TABLE 3

| | Iodine Staining (CIE L*) | | Bleaching (CIE L*) | |
|---|---|---|---|---|
| | Ave | Stdev | Ave | Stdev |
| Buffer Control | 26.10 | 2.25 | 87.33 | 0.20 |
| (−) Enzymes | 24.42 | 0.23 | 90.46 | 0.18 |
| (+) Enzymes | 33.93 | 1.25 | 93.54 | 0.23 |

Example 3

Laccase enzyme from *Cerrena unicolor*, as described in PCT Application No. WO 2008/076322, was encapsulated in Elvanol 52-22 polyvinyl alcohol (88% hydrolysis, 1300 nominal degree of polymerization), which dissolves in water at room temperature. The polymeric film contained 1.5 mass-% laccase, 8.5 mass-% non-enzyme ultrafiltration concentrate solids from fermentation, and 90 mass-% polymer. Circular disks 5/32 in. in diameter were cut from the PVA film containing encapsulated laccase enzyme ("PVA laccase disks"). The enzyme was encapsulated in the polymer as described in Example 1.

Enzyme Leaching

Enzyme leaching from the PVA laccase disks was assessed using three different laccase mediators as substrates for the enzyme.

1. ABTS

Figure 2:
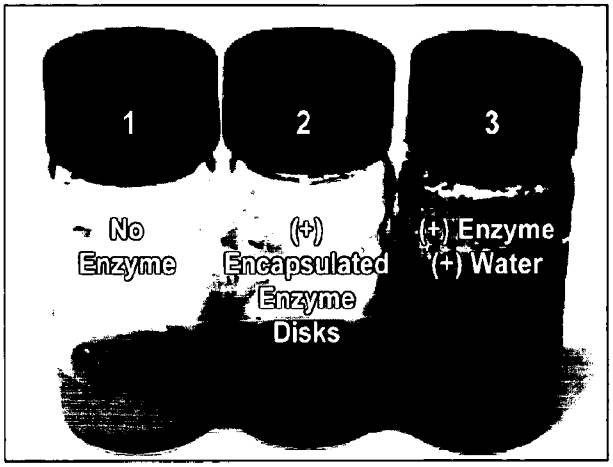
FIG. 2 shows the results of the enzyme leaching experiment with PVA laccase disks and ABTS laccase mediator, as described in Example 3.

Two PVA laccase disks were inserted into a glass vial with a solution of 1 ml of PGDA containing 1% by weight ABTS (diammonium 2,2'-azino-bis(3-ethylbenzothiazoline-6-sulfonate) and incubated for 10 days at room temperature (vial "2" in FIG. 2). The same preparation without PVA laccase disks was prepared as a negative control (vial "1" in FIG. 2). In addition, two PVA laccase disks were dissolved in 100 μl of deionized water and then added to a vial containing 1 ml PGDA with 1% ABTS as a positive control (vial "3" in FIG. 2). Color changes of these solutions were monitored as an indication of enzyme leaching.

After 10 days of incubation at room temperature, no color changes were observed in vials 1 and 2. However the solution color in vial 3 changed to dark green as soon as the dissolved laccase was added to the vial, indicating laccase and mediator reaction.

2. SA

Figure 3:
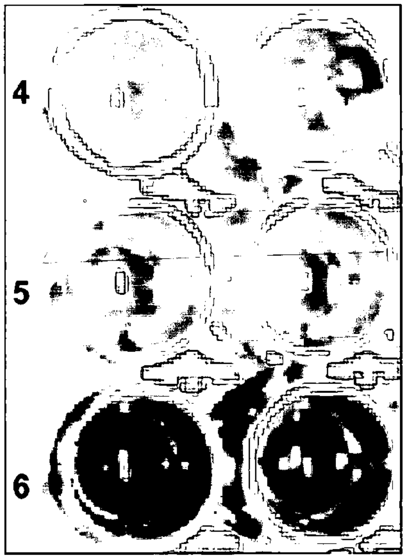
FIG. 3 shows the results of the enzyme leaching experiment with PVA laccase disks and SA laccase mediator, as described in Example 3.

Two PVA laccase disks were inserted into a glass vial with a solution of 1 ml of PGDA containing 1% by weight syringamide (3,5-dimethoxy-4-hydroxybenzamide; "SA") and incubated for 10 days at room temperature ("4" in FIG. 3). The same preparation without PVA laccase disks was prepared as a negative control ("5" in FIG. 3). In addition, two PVA laccase disks were dissolved in 100 μl of deionized water and then added to a vial containing 1 ml PGDA with 1% SA as a positive control ("6" in FIG. 3).

The color of the solution containing dissolved laccase ("6") changed from light yellow to brown, indicating laccase reacted with the mediator. However, the same preparation with encapsulated enzyme disks ("4") did not change color over the 10 day incubation and these results suggest that the encapsulated laccase did not react with SA in the PGDA solution.

After 10 days of incubation at room temperature, the incubated solutions were centrifuged and the absorbance was measured at 420 nm in a spectrophotometer. The results are shown in Table 4.

TABLE 4

| | | Absorbance (420 nm) | | | |
|---|---|---|---|---|---|
| | | 1 | 2 | Ave | Stdev |
| 4 | PGDA + SA | 0.1980 | 0.1993 | 0.1987 | 0.0009 |
| 5 | PGDA + SA + 2 Enz Disks | 0.2028 | 0.2048 | 0.2038 | 0.0014 |
| 6 | PGDA + SA + 2 Enz Disks + 100 ml Water | 1.0357 | 1.0433 | 1.0395 | 0.0054 |

3. SN

Figure 4:
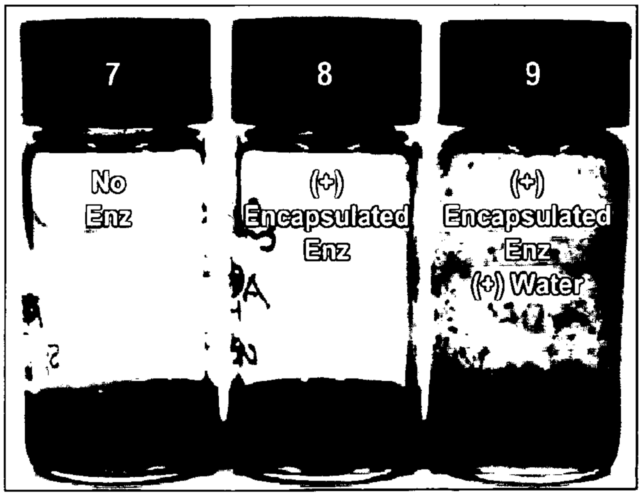
FIG. 4 shows the results of the enzyme leaching experiment with PVA laccase disks and SN laccase mediator, as described in Example 3.

Two PVA laccase disks were inserted into a glass vial with a solution of 1 ml of PGDA containing 5% by weight syringonitrile (3,5-dimethoxy-4-hydroxybenzonitrile; "SN") and incubated for 10 days at room temperature ("8" in FIG. 4). The same preparation without PVA laccase disks was prepared as a negative control ("7" in FIG. 4). In addition, two PVA laccase disks were dissolved in 100 μl of deionized water and then added to a vial containing 1 ml PGDA with 1% SN as a positive control ("9" in FIG. 4).

Within 1 hour, the color of vial 9 changed to a greenish brown color, indicating laccase reacted with SN. The color of vials 7 and 8 remained unchanged over the 10 day incubation period.

Application Testing

Denim Preparation

Desized sulfur bottom/indigo dyed denim and desized 100% indigo dyed denim were treated in a Unimac (501b lab scale) tumbling washer with 1 g/L INDIAGE® 44L cellulase at 55° C. and pH 4.8 for 60 minutes at a 10:1 liquor ratio followed by two rinses and then dried.

For the 12 well microtiter plate experiments described below, ⅝-inch diameter round fabric swatches were cut from the cellulase pretreated denim fabric. For the Launder-Ometer experiments described below, 3 in.×4 in. fabric swatches were cut from the cellulase pretreated denim fabric and then the edges were sewed to prevent fraying during the treatment.

Evaluation of Bleaching Performance

To quantify bleaching effects, reflectometer readings of each denim fabric swatch were taken before and after treatment using a Chroma Meter CR-200 by Minolta. The total color difference (ΔE) was calculated according to the following formula:

$$\text{Total color difference}(\Delta E)=\sqrt{(\Delta L^2+\Delta a^2+\Delta b^2)}$$

(where ΔL, Δa, Δb, are differences in CIE L*, CIE a*, and CIE b* values respectively, before and after the laccase bleaching).

12 well Microtiter Plate Experiments

⅝-inch diameter pretreated denim swatches were incubated in a 12-well microtiter plate under the following conditions:

1. Buffer only
2. Buffer+50 μl of PGDA solution containing 5% SN
3. Buffer+50 μl of PGDA solution containing 5% SN+encapsulated laccase 12 well micro titer plate assay (2 ml reaction volume)

pH: 6 (50 mM sodium acetate buffer in water)

Temperature: 60° C.

Incubation time: 60 minutes

Enzyme: 5, 5/32" inch disks of laccase encapsulated film per test

Mediator: 50 μl of PGDA solution containing 5% syringonitrile per test

Figure 5:
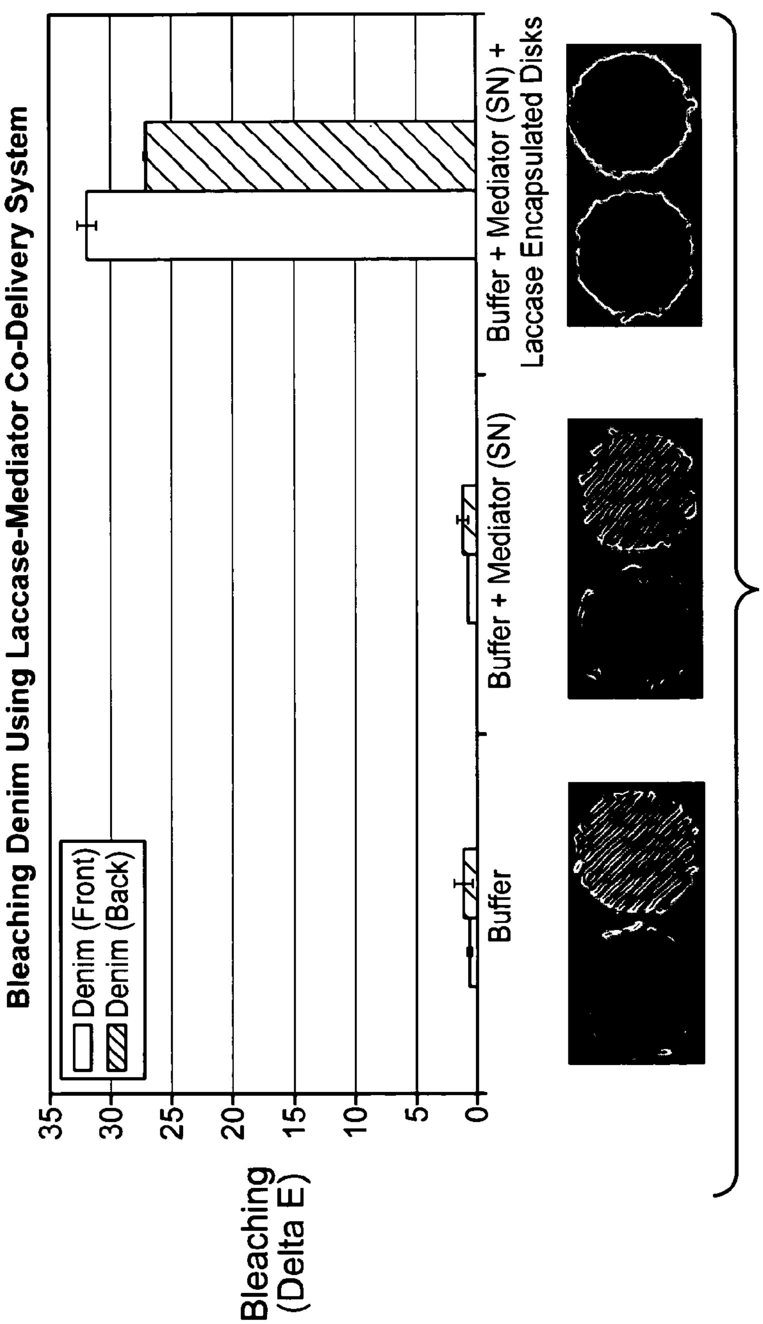
FIG. 5 shows the results of denim bleaching in the 12 well microtiter plate experiments described in Example 3.

The results are shown in FIG. 5. A dramatic bleaching effect was observed when the denim swatches were incubated with PVA laccase disks. The results clearly indicated that water triggered release of the laccase from the polymeric film in which it was encapsulated, providing access to the mediator and resulting in reaction of the enzyme with the mediator to cause bleaching.

Launder-Ometer Experiments 3 in×4 in. cellulase pretreated denim swatches were incubated in a Launder-Ometer under the following conditions:

(A) 1 ml PGDA solution containing 5% SN (B) 1 ml PGDA solution containing 5% SN and 0.15 g encapsulated laccase (C) 1 ml PGDA solution containing 5% ABTS (D) 1 ml PGDA solution containing 5% ABTS and 0.15 g encapsulated laccase Launder-Ometer (250 ml total reaction volume)

pH: 6 (50 mM sodium acetate buffer in water)

Temperature: 60° C.

Incubation time: 60 minutes

Enzyme: 0.15 g encapsulated laccase film cut into small random pieces

Mediator:

Syringonitrile (SN)

Diammonium 2,2'-azino-bis(3-ethylbenzothiazoline-6-sulfonate) (ABTS)

Figure 6:
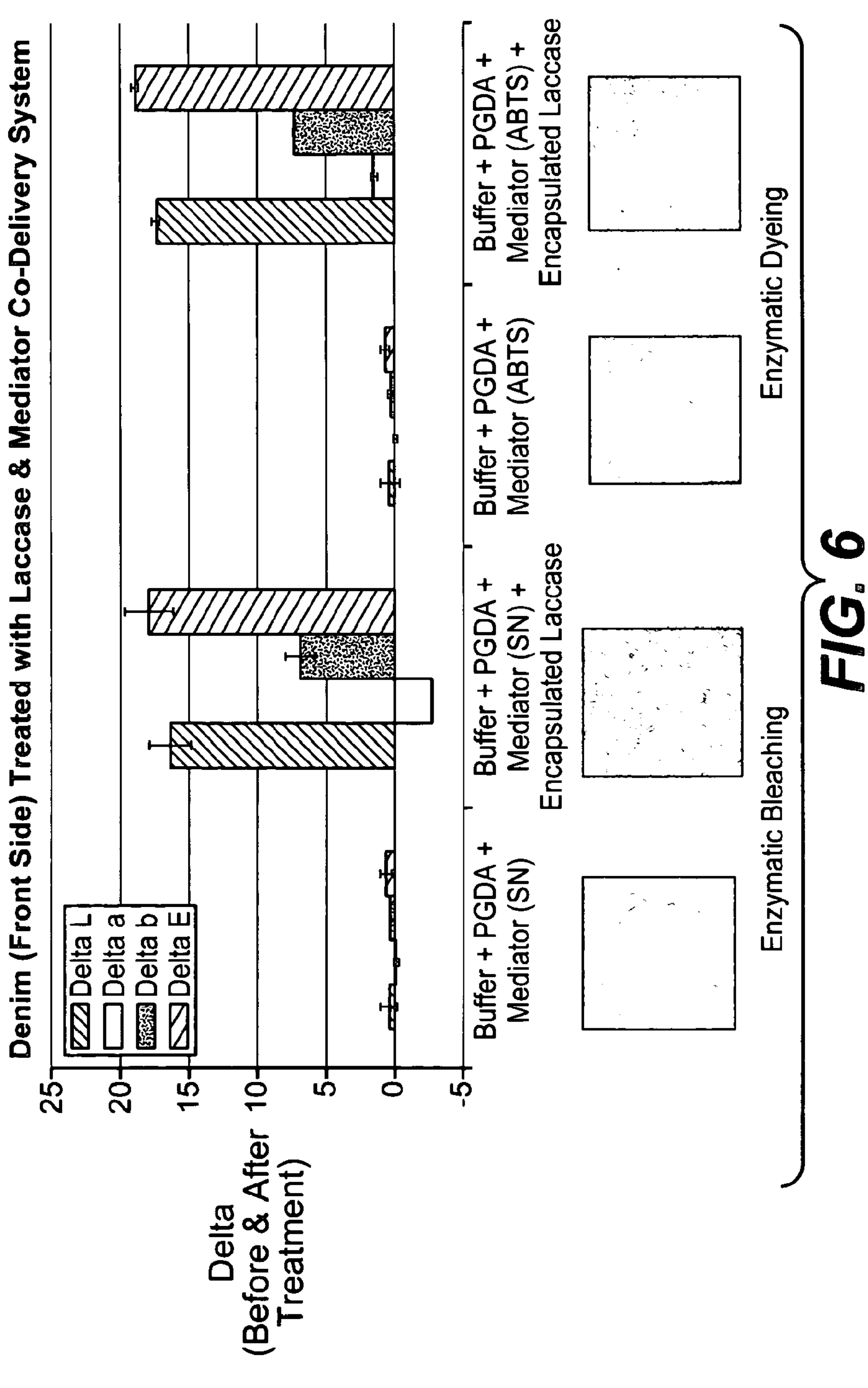
FIG. 6 shows the results of denim bleaching and dyeing in the Launder-Ometer experiments described in Example 3.

The results are shown in Table 5 and FIG. 6. The denim swatches treated with preparation (B) (laccase+SN co-delivery system) were significantly bleached. The color of the denim swatches treated with preparation (D) (laccase+ABTS co-delivery system) dyed into a light purple color.

2. Thaw out one 500 μL aliquot of ABTS stock and add to the citric acid solution.

TABLE 5

| | Color Difference Between Before and After the Treatments | | | | | | | |
|---|---|---|---|---|---|---|---|---|
| | Delta L | | Delta a | | Delta b | | Delta E: | |
| | Ave | Stdev | Ave | Stdev | Ave | Stdev | Ave | Stdev |
| Buffer + PGDA + Mediator (SN) | 0.38 | 0.62 | −0.15 | 0.18 | 0.37 | 0.02 | 0.65 | 0.41 |
| Buffer + PGDA + Mediator (SN) + Encapsulated Laccase | 16.35 | 1.49 | −2.78 | 0.06 | 6.89 | 1.04 | 17.96 | 1.76 |
| Buffer + PGDA + Mediator (ABTS) | 0.32 | 0.71 | −0.07 | 0.15 | 0.29 | 0.11 | 0.64 | 0.32 |
| Buffer + PGDA + Mediator (ABTS) + Encapsulated Laccase | 17.41 | 0.28 | 1.45 | 0.25 | 7.31 | 0.06 | 18.94 | 0.26 |

Example 4

Stabilized Enzyme Bleaching System

This example demonstrates how encapsulation of enzyme within a polymer matrix can be used to stabilize a single-bottle enzymatic bleaching or disinfection system. The single-bottle system is designed to produce peracetic acid upon dilution with water. Its components are: sodium perborate, propylene glycol diacetate (PGDA) and arylesterase (ArE) and a nonaqueous carrier fluid. In this embodiment, the carrier fluid was an alcohol ethoxylate nonionic surfactant (Novel 1012-6 from Sasol Co.; Hamburg, Del.).

The ArE enzyme component was added to the system in two ways: (1) directly from a liquid enzyme concentrate, and (2) encapsulated in polymer as a spray dried powder. The polymer was hydroxypropyl methylcellulose (HPMC, Methocel E5 Premium LV from Dow Chemical Co., Midland, Mich., USA). The spray drying was conducted such that the dried powder was 75% (by mass) HPMC.

For both the enzyme concentrate and the encapsulated enzyme, 12.5 μg of active ArE was added to each of six test tubes containing 1 g of carrier fluid, 135 mg of sodium perborate, and 2 mg of PGDA. For each set of six tubes, three of the tubes were triggered (by dilution with 9 ml Tris, pH 9.0, buffer) and assayed for peracetic acid as described below. The other three tubes were incubated at 37° C. for five days, then triggered and assayed for peracetic acid.

Assay for Peracetic Acid

Materials and Methods:

Peracetic acid: Sigma-Fluka P/N 77240; L/N 11244491, 38.8% (5.115M, F.W.=76.05 g/mol), peracetic acid as per C of A.

2,2'-Azino-bis(3-ethylbenzothiazoline-6-sulfonic acid) diammonium salt (ABTS): Fluka P/N WA10917, L/N 1135552 54804068, 99+% pure (HPLC), F.W.=548.64 g/mol Citric Acid: Sigma P/N C1857, L/N 00541(0001, F.W.=192.13

Potassium iodide (KI): P/N Sigma P4286, L/N 1241(0151, F.W.=166.0

Stock Solutions:

125 mM citric acid, pH to 5.0 with NaOH, sterile filter 0.22 μm, stable indefinitely at room temperature until growth apparent (usually fungi at this pH)

100 mM ABTS in Milli Q (MQ) $H_2O$. Aliquot in 500 μL aliquots and store at −20° C. for up to six months.

25 mM KI in MQ $H_2O$, Stable indefinitely at room temperature.

Working Substrate:

1. Add 50 mL of stock 125 mM citric acid buffer to a light-proof container (an aluminum foil wrapped glass bottle is acceptable)

3. Add 100 μL of 25 mM KI to the citric acid.

4. Swirl gently to mix and cap. Solution good for up to 54 hours when stored in the dark at room temperature.

Preparation of Standard Curve:

1. Obtain stock peracetic acid (usually ~39%; ~390 g/L; 390 (g/L)/76.05 (g/mole) ~5.13 M. NOTE: this actual concentration will be determined by the actual assay number reported on the CofA.

2. Make a 1:100 dilution of stock PAA into 125 mM citric acid. Cap and vortex for 15 seconds.

3. Take the 1:100 dilution from step 2 and dilute it 1:100 (this would make a 1:10000 dilution of the stock PAA) into 125 mM citric acid. Cap and vortex for 15 seconds. This concentration of PAA is now ~5000 mM/10000=~0.5 mM=~500 uM 4. Take the solution from step three and dilute 4 parts standard (the ~500 uM standard from #3) to 1 part citric acid to make a standard around 400 uM 5. Take the solution from step three and dilute 3 parts standard (the ~500 uM standard from #3) to 2 parts citric acid to make a standard around 300 uM 6. Take the solution from step three and dilute 2 parts standard (the ~500 uM standard from #3) to 3 parts citric acid to make a standard around 200 uM 7. Take the solution from step three and dilute 1 part standard (the ~500 uM standard from #3) to 4 parts citric acid to make a standard around 100 uM Assay:

1. In a microtiter plate, place 20 μl of all standards, in descending dilution order in triplicate either in row format or column format (one standard per well).

2. At the end of the standard curve, place 20 μl of citric acid into triplicate wells (these are the blanks).

3. In separate rows or columns place 20 μl of diluted samples into triplicate wells.

4. Pour out a suitable amount of working substrate into a substrate basin (or clean Petri dish lid or base, or a clean pipet tip box lid)

5. With a multichannel pipet, add 200 μl of substrate to each well of the microtiter plate that has standard, blank and sample.

6. With a timer, let the reaction proceed for 3 minutes (+/−0.5 min)

7. Read wells in a microplate reader @ 420 nm

8. Transfer the data into Excel or use the plate reader program to generate standard curve, calculate slope and calculate y-intercept by linear regression using the standards data (calculate mean, SD, etc).

9. Calculate sample concentrations using the slope and intercept using y=m*x+b and multiplying by sample dilution factor.

Results

The peracetic acid results for each set of three tubes were averaged and tabulated. The results are shown in Table 6. The encapsulated sample demonstrated significantly increased stability after 5 days at 37° C.

TABLE 6

| Sample | Peracetic acid produced (μM) No incubation | After 5 days at 37° C. |
| --- | --- | --- |
| Enzyme concentrate | 410 | 153 |
| Enzyme encapsulated in polymer | 417 | 275 |

Although the foregoing invention has been described in some detail by way of illustration and examples for purposes of clarity of understanding, it will be apparent to those skilled in the art that certain changes and modifications may be practiced without departing from the spirit and scope of the invention. Therefore, the description should not be construed as limiting the scope of the invention.

All publications, patents, and patent applications cited herein are hereby incorporated by reference in their entireties for all purposes and to the same extent as if each individual publication, patent, or patent application were specifically and individually indicated to be so incorporated by reference.

What is claimed is:

1. A liquid delivery system for co-formulated enzyme and substrate, wherein the delivery system is a composition comprising: an enzyme and a substrate for the enzyme, wherein the enzyme is encapsulated in a water-soluble polymeric matrix, wherein the substrate is present in a substantially non-aqueous liquid phase comprising less than about 5% water, which is in contact with the polymeric matrix in which the enzyme is encapsulated, and wherein the polymer is not soluble in the liquid phase.

2. The delivery system of claim 1, wherein the substantially non-aqueous liquid phase comprises less than about 1% water.

3. The delivery system of claim 1, wherein the substantially non-aqueous liquid phase comprises less than about 0.5% water.

4. The delivery system of claim 1, wherein the enzyme retains catalytic potential in the polymeric matrix but substantially does not react with the substrate in the composition for at least 10 days at 25° C.

5. The delivery system of claim 1, wherein following addition of water to the composition, the polymeric matrix is solubilized, releasing the enzyme, and permitting catalytic reaction with the substrate to occur.

6. The delivery system of claim 1, comprising one or more enzymes selected from the group consisting of proteases, cellulases, amylases, pectinases, perhydrolases, peroxidases, carbohydrate oxidases, phenol oxidizing enzymes, cutinases, lipases, hemicellulases, xylanases, mannanases, catalases, laccases, and mixtures thereof.

7. The delivery system of claim 1, comprising two or more enzymes encapsulated in the same polymeric matrix.

8. The delivery system of claim 1, comprising two or more enzymes encapsulated in separate polymeric matrices.

9. The delivery system of claim 1, further comprising at least one surfactant.

10. The delivery system of claim 1, wherein the polymeric matrix is selected from the group consisting of polyvinyl alcohol, methylcellulose, hydroxypropyl methylcellulose, polyvinyl pyrrolidone, guar gum, and derivatives or co-polymers thereof.

11. The delivery system of claim 1, wherein the enzyme encapsulated in a polymeric matrix in the form of particles is suspended in a substantially non-aqueous liquid containing the substrate.

12. The delivery system of claim 11, wherein the particles are held in suspension by a suspending aid.

13. The delivery system of claim 1, wherein the substrate is solubilized or dispersed in a substantially non-aqueous liquid phase, which may optionally include a non-aqueous liquid (carrier fluid).

14. The delivery system of claim 13, wherein the carrier fluid is selected from the group consisting of glycols, nonionic surfactants, alcohols, polglycols, acetate esters, and a mixture thereof.

15. The delivery system of claim 13, wherein the carrier fluid is a substrate for the enzyme.

16. The delivery system of claim 1, wherein the enzyme is a perhydrolase and the substrate is an ester substrate.

17. The delivery system of claim 1, wherein the enzyme is a perhydrolase and the substrate propylene glycol diacetate.

18. The delivery system of claim 1, further comprising a hydrogen peroxide generating compound selected from sodium percarbonate, sodium perborate, and urea hydrogen peroxide, wherein a peracid is produced after water is added to the composition.

19. The delivery system of claim 1, wherein the enzyme is a laccase enzyme, and the substrate is a laccase mediator.

20. The delivery system of claim 1, wherein the enzyme is a phenol oxidizing enzyme, and the substrate is selected from the group consisting of 2,2'-azino-bis(3-ethylbenzothiazoline-6-sulfonate), syringamide, and syringonitrile.

21. The delivery system of claim 1, wherein the enzyme is a perhydrolase and the substrate is an ester substrate, and the delivery system further comprises sodium perborate.

22. The delivery system of claim 21, wherein the delivery system increased storage stability compared to a comparable delivery system lacking the polymer.

23. A kit containing the delivery system for co-formulated enzyme and substrate according to claim 1 and instructions for use.

24. A method for bleaching a textile, comprising: (a) adding the delivery system of claim 16 to water in the presence of a hydrogen peroxide source and mixing, thereby generating an aqueous peracid solution; and (b) contacting a textile with the solution for a length of time and under conditions suitable to permit measurable whitening of the textile, thereby producing a bleached textile.

25. A method for decontamination, comprising: (a) adding the delivery system of claim 16 to water in the presence of a hydrogen peroxide source and mixing, thereby generating an aqueous peracid solution; and (b) contacting an item comprising a contaminant with the solution, thereby reducing the concentration of the contaminant.

26. The method of claim 24, wherein the hydrogen peroxide source is sodium perborate.

* * * * *

```
                         SEQUENCE LISTING


<160> NUMBER OF SEQ ID NOS: 3

<210> SEQ ID NO 1
<211> LENGTH: 505
<212> TYPE: PRT
<213> ORGANISM: Mycobacterium smegmatis

<400> SEQUENCE: 1

Ala Ile Gly Pro Val Ala Asp Leu His Ile Val Asn Lys Asp Leu Ala
1               5                   10                  15

Pro Asp Gly Val Gln Arg Pro Thr Val Leu Ala Gly Gly Thr Phe Pro
            20                  25                  30

Gly Thr Leu Ile Thr Gly Gln Lys Gly Asp Asn Phe Gln Leu Asn Val
        35                  40                  45

Ile Asp Asp Leu Thr Asp Asp Arg Met Leu Thr Pro Thr Ser Ile His
    50                  55                  60

Trp His Gly Phe Phe Gln Lys Gly Thr Ala Trp Ala Asp Gly Pro Ala
65                  70                  75                  80

Phe Val Thr Gln Cys Pro Ile Ile Ala Asp Asn Ser Phe Leu Tyr Asp
                85                  90                  95

Phe Asp Val Pro Asp Gln Ala Gly Thr Phe Trp Tyr His Ser His Leu
            100                 105                 110

Ser Thr Gln Tyr Cys Asp Gly Leu Arg Gly Ala Phe Val Val Tyr Asp
        115                 120                 125

Pro Asn Asp Pro His Lys Asp Leu Tyr Asp Val Asp Asp Gly Gly Thr
    130                 135                 140

Val Ile Thr Leu Ala Asp Trp Tyr His Val Leu Ala Gln Thr Val Val
145                 150                 155                 160

Gly Ala Ala Thr Pro Asp Ser Thr Leu Ile Asn Gly Leu Gly Arg Ser
                165                 170                 175

Gln Thr Gly Pro Ala Asp Ala Glu Leu Ala Val Ile Ser Val Glu His
            180                 185                 190

Asn Lys Arg Tyr Arg Phe Arg Leu Val Ser Ile Ser Cys Asp Pro Asn
        195                 200                 205

Phe Thr Phe Ser Val Asp Gly His Asn Met Thr Val Ile Glu Val Asp
    210                 215                 220

Gly Val Asn Thr Arg Pro Leu Thr Val Asp Ser Ile Gln Ile Phe Ala
225                 230                 235                 240

Gly Gln Arg Tyr Ser Phe Val Leu Asn Ala Asn Gln Pro Glu Asp Asn
                245                 250                 255

Tyr Trp Ile Arg Ala Met Pro Asn Ile Gly Arg Asn Thr Thr Thr Leu
            260                 265                 270

Asp Gly Lys Asn Ala Ala Ile Leu Arg Tyr Lys Asn Ala Ser Val Glu
        275                 280                 285

Glu Pro Lys Thr Val Gly Gly Pro Ala Gln Ser Pro Leu Asn Glu Ala
    290                 295                 300
```

```
Asp Leu Arg Pro Leu Val Pro Ala Pro Val Pro Gly Asn Ala Val Pro
305                 310                 315                 320

Gly Gly Ala Asp Ile Asn His Arg Leu Asn Leu Thr Phe Ser Asn Gly
                325                 330                 335

Leu Phe Ser Ile Asn Asn Ala Ser Phe Thr Asn Pro Ser Val Pro Ala
            340                 345                 350

Leu Leu Gln Ile Leu Ser Gly Ala Gln Asn Ala Gln Asp Leu Leu Pro
        355                 360                 365

Thr Gly Ser Tyr Ile Gly Leu Glu Leu Gly Lys Val Val Glu Leu Val
    370                 375                 380

Ile Pro Pro Leu Ala Val Gly Gly Pro His Pro Phe His Leu His Gly
385                 390                 395                 400

His Asn Phe Trp Val Val Arg Ser Ala Gly Ser Asp Glu Tyr Asn Phe
                405                 410                 415

Asp Asp Ala Ile Leu Arg Asp Val Val Ser Ile Gly Ala Gly Thr Asp
            420                 425                 430

Glu Val Thr Ile Arg Phe Val Thr Asp Asn Pro Gly Pro Trp Phe Leu
        435                 440                 445

His Cys His Ile Asp Trp His Leu Glu Ala Gly Leu Ala Ile Val Phe
    450                 455                 460

Ala Glu Gly Ile Asn Gln Thr Ala Ala Ala Asn Pro Thr Pro Gln Ala
465                 470                 475                 480

Trp Asp Glu Leu Cys Pro Lys Tyr Asn Gly Leu Ser Ala Ser Gln Lys
                485                 490                 495

Val Lys Pro Lys Lys Gly Thr Ala Ile
            500                 505


<210> SEQ ID NO 2
<211> LENGTH: 216
<212> TYPE: PRT
<213> ORGANISM: Mycobacterium smegmatis

<400> SEQUENCE: 2

Met Ala Lys Arg Ile Leu Cys Phe Gly Asp Ser Leu Thr Trp Gly Trp
1               5                   10                  15

Val Pro Val Glu Asp Gly Ala Pro Thr Glu Arg Phe Ala Pro Asp Val
            20                  25                  30

Arg Trp Thr Gly Val Leu Ala Gln Gln Leu Gly Ala Asp Phe Glu Val
        35                  40                  45

Ile Glu Glu Gly Leu Ser Ala Arg Thr Thr Asn Ile Asp Asp Pro Thr
    50                  55                  60

Asp Pro Arg Leu Asn Gly Ala Ser Tyr Leu Pro Ser Cys Leu Ala Thr
65                  70                  75                  80

His Leu Pro Leu Asp Leu Val Ile Ile Met Leu Gly Thr Asn Asp Thr
                85                  90                  95

Lys Ala Tyr Phe Arg Arg Thr Pro Leu Asp Ile Ala Leu Gly Met Ser
            100                 105                 110

Val Leu Val Thr Gln Val Leu Thr Ser Ala Gly Gly Val Gly Thr Thr
        115                 120                 125

Tyr Pro Ala Pro Lys Val Leu Val Val Ser Pro Pro Pro Leu Ala Pro
    130                 135                 140

Met Pro His Pro Trp Phe Gln Leu Ile Phe Glu Gly Gly Glu Gln Lys
145                 150                 155                 160

Thr Thr Glu Leu Ala Arg Val Tyr Ser Ala Leu Ala Ser Phe Met Lys
```

-continued

```
            165                 170                 175

Val Pro Phe Phe Asp Ala Gly Ser Val Ile Ser Thr Asp Gly Val Asp
        180                 185                 190

Gly Ile His Phe Thr Glu Ala Asn Asn Arg Asp Leu Gly Val Ala Leu
    195                 200                 205

Ala Glu Gln Val Arg Ser Leu Leu
210                 215


<210> SEQ ID NO 3
<211> LENGTH: 651
<212> TYPE: DNA
<213> ORGANISM: Mycobacterium smegmatis

<400> SEQUENCE: 3

atggccaagc gaattctgtg tttcggtgat tccctgacct ggggctgggt ccccgtcgaa      60

gacggggcac ccaccgagcg gttcgccccc gacgtgcgct ggaccggtgt gctggcccag     120

cagctcggag cggacttcga ggtgatcgag gagggactga gcgcgcgcac caccaacatc     180

gacgacccca ccgatccgcg gctcaacggc gcgagctacc tgccgtcgtg cctcgcgacg     240

cacctgccgc tcgacctggt gatcatcatg ctgggcacca acgacaccaa ggcctacttc     300

cggcgcaccc cgctcgacat cgcgctgggc atgtcggtgc tcgtcacgca ggtgctcacc     360

agcgcgggcg gcgtcggcac cacgtacccg gcacccaagg tgctggtggt ctcgccgcca     420

ccgctggcgc ccatgccgca cccctggttc cagttgatct tcgagggcgg cgagcagaag     480

accactgagc tcgcccgcgt gtacagcgcg ctcgcgtcgt tcatgaaggt gccgttcttc     540

gacgcgggtt cggtgatcag caccgacggc gtcgacggaa tccacttcac cgaggccaac     600

aatcgcgatc tcggggtggc cctcgcggaa caggtgcgga gcctgctgta a              651
```